United States Patent [19]

Fuchs et al.

[11] Patent Number: 5,070,098
[45] Date of Patent: Dec. 3, 1991

[54] SUBSTITUTED PYRAZOLINE DERIVATIVES, PESTICIDAL COMPOSITIONS AND USE

[75] Inventors: Rainer Fuchs, Wuppertal; Ulrike Wachendorff-Neumann, Monheim; Benedikt Becker, Appiano; Christoph Erdelen, Leichlingen; Wilhelm Stendel, Wuppertal, all of Fed. Rep. of Germany

[73] Assignee: Bayer Aktiengesellschaft, Leverkusen, Fed. Rep. of Germany

[21] Appl. No.: 641,417

[22] Filed: Jan. 15, 1991

[30] Foreign Application Priority Data

Jan. 24, 1990 [DE] Fed. Rep. of Germany ....... 4001931
Oct. 10, 1990 [DE] Fed. Rep. of Germany ....... 4032089

[51] Int. Cl.$^5$ ................. A01N 43/56; A01N 43/647; C07D 403/04; C07D 403/14
[52] U.S. Cl. ........................... 514/359; 514/381; 514/382; 514/383; 514/394; 514/397; 514/403; 514/406; 514/63; 424/45; 424/46; 548/110; 548/253; 548/255; 548/266.2; 548/265.6; 548/336; 548/371; 548/374; 548/379; 548/264.8; 548/327

[58] Field of Search .............. 548/264.8, 371, 110, 548/253, 255, 266.2, 265.6, 327, 336, 374, 379; 514/63, 359, 381, 382, 383, 394, 397, 403, 406; 424/45, 46

[56] References Cited

U.S. PATENT DOCUMENTS 3,991,073 11/1976 Mulder et al. .................. 548/379
4,070,365 1/1978 van Daalen et al. ............ 548/379

Primary Examiner—Robert W. Ramsuer
Attorney, Agent, or Firm—Sprung Horn Kramer & Woods

[57] ABSTRACT

This invention relates to novel substituted pyrazoline derivatives of the general formula

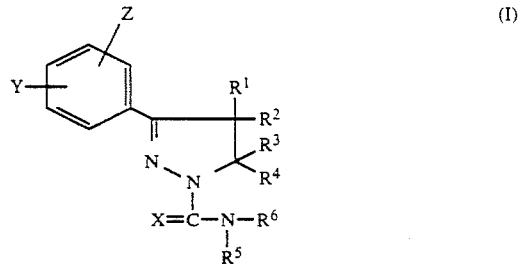

processes for their preparation and their use as pesticides.

5 Claims, No Drawings

SUBSTITUTED PYRAZOLINE DERIVATIVES, PESTICIDAL COMPOSITIONS AND USE

BACKGROUND OF THE INVENTION

The invention relates to new substituted pyrazoline derivatives, to processes for their preparation, and to their use as pesticides.

It is known that certain substituted pyrazoline derivatives have a good activity against animal pests.

In this context, see, for example, DE-A 2,700,258, U.S. Pat. No. 4,174,393, DE-A 2,529,689 and US-A 4,070,365.

However, the level of action, or duration of action, of these previously known compounds is not entirely satisfactory in all fields of use, in particular against certain organisms or when low concentrations are used.

SUMMARY OF THE INVENTION

New substituted pyrazoline derivatives have been found, of the general formula

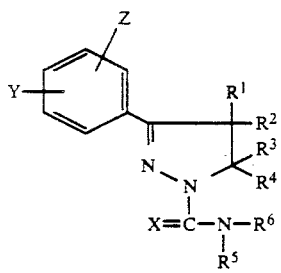

(I)

in which $R^1$ represents an unsaturated five-membered heterocycle which contains 1 to 4 nitrogen atoms, which is optionally substituted and which is optionally benzo-fused, $R^2$ represents hydrogen, alkyl, optionally substituted cycloalkyl, halogenoalkyl, halogenoalkylthio or alkoxycarbonyl or trialkylsilyl, $R^3$ represents hydrogen or alkyl, $R^4$ represents hydrogen or alkyl, $R^5$ represents hydrogen, alkyl, phenyl or alkylthio, $R^6$ represents optionally substituted alkyl or optionally substituted cycloalkyl, or represents the radical

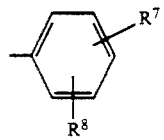

where $R^7$ and $R^8$ can be identical or different and represent hydrogen, halogen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylthionyl, alkylsulphonyl, halogenoalkylthionyl, halogenoalkylsulphonyl or halogenoalkoxycarbonyl, or where $R^7$ and $R^8$ together represent a bivalent radical which optionally contains one or two oxygen atoms and which is optionally substituted, X represents oxygen or sulphur and Y and Z can be identical or different and represent hydrogen, alkyl, halogen, halogenoalkyl, alkoxy, alkylthio, halogenoalkoxy, halogenoalkylthio, alkoxycarbonyl, halogenoalkoxycarbonyl, optionally substituted aryloxy, optionally substituted arylthio, alkenyloxy, alkinyl, alkylthionyl, alkylsulphonyl, halogenoalkylthionyl, halogenoalkylsulphonyl, amino, nitro or cyano, or where Y and Z together represent optionally halogen-substituted 3,4-methylenedioxy or 3,4-ethylenedioxy.

Furthermore, it has been found that the new substituted pyrazoline derivatives of the general formula (I)

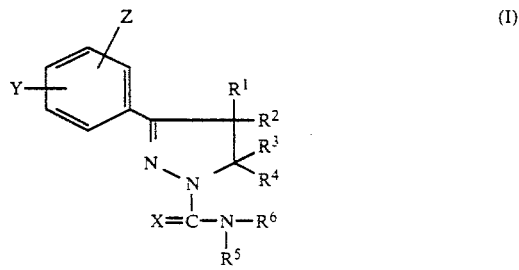

in which $R^1$ represents an unsaturated five-membered heterocycle which contains 1 to 4 nitrogen atoms, which is optionally substituted and which is optionally benzo-fused, $R^2$ represents hydrogen, alkyl, optionally substituted cycloalkyl, halogenoalkyl, halogenoalkylthio, alkoxycarbonyl or trialkylsilyl, $R^3$ represents hydrogen or alkyl, $R^4$ represents hydrogen or alkyl, $R^5$ represents hydrogen, alkyl, phenyl or alkylthio, $R^6$ represents optionally substituted alkyl or optionally substituted cycloalkyl, or represents the radical

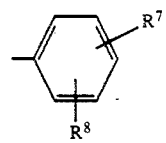

where $R^7$ and $R^8$ can be identical or different and represent hydrogen, halogen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylthionyl, alkylsulphonyl, halogenoalkylthionyl, halogenoalkylsulphonyl or halogenoalkoxycarbonyl, or where $R^7$ and $R^8$ together represent a bivalent radical which optionally contains one or two oxygen atoms and which is optionally substituted, X represents oxygen or sulphur and Y and Z can be identical or different and represent hydrogen, alkyl, halogen, halogenoalkyl, alkoxy, alkylthio, halogenoalkoxy, halogenoalkylthio, alkoxycarbonyl, halogenoalkoxycarbonyl, optionally substituted aryloxy, optionally substituted arylthio, alkenyloxy, alkinyl, alkylthionyl, alkylsulphonyl, halogenoalkylthionyl, halogenoalkylsulphonyl, amino, nitro or cyano, or where Y and Z together represent optionally halogen-substituted 3,4-methylenedioxy or 3,4-ethylenedioxy, are obtained when (a) to obtain pyrazoline derivatives of the formula (I) in which $R^5$ represents hydrogen, pyrazoline derivatives of the formula (II)

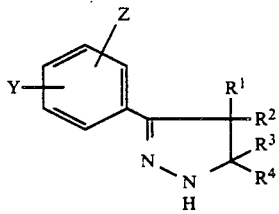

in which Y, Z, $R^1$, $R^2$, $R^3$ and $R^4$ have the above-mentioned meaning are reacted with isocyanates or isothiocyanates of the formula (III)

in which X and $R^6$ have the abovementioned meaning, if appropriate in the presence of bases, or when (b) to obtain pyrazoline derivatives of the formula (I) in which $R^2$ represents alkyl, cycloalkyl, halogenoalkyl, halogenoalkylthio, alkoxycarbonyl or trialkylsilyl, compounds of the formula (IV)

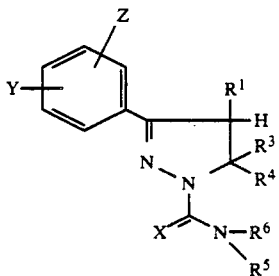

are reacted with compounds of the formula (V)

in which

Hal represents halogen and $R^9$ represents alkyl, cycloalkyl, halogenoalkyl, halogenoalkylthio or alkoxycarbonyl, in an anhydrous medium with the addition of a strong base.

Finally, it has been found that the new pyrazoline derivatives of the general formula (I) have a very good activity against pests and, in particular, have a very good insecticidal and acaricidal activity.

Surprisingly, the substituted pyrazoline derivatives according to the invention have a considerably more powerful insecticidal activity against insects and arachnids which damage plants and parasitize warm-blooded animals than compounds which are similar chemically and from the point of view of their action and which are known from the prior art.

DESCRIPTION OF THE PREFERRED EMBODIMENTS

Formula (I) provides a general definition of the substituted pyrazoline derivatives according to the invention. Preferred compounds of the formula (I) are those in which $R^1$ represents a 1H-pyrrol-1-yl, 1H-pyrazol-1-yl, 1H-imidazol-1-yl, 2H-1,2,3,-triazol-2-yl, 1H-1,2,3-triazol-1-yl, 1H-1,2,4,-triazol-1-yl, 4H-1,2,4-triazol-4-yl, 2H-tetrazol-2-yl or 1H-tetrazol-2-yl radical, each of which is optionally substituted by halogen, alkyl($C_1-C_6$), CN, $NO_2$, alkoxy($C_1-C_6$)carbonyl, alkyl($C_1-C_4$)thio, alkoxy($C_1-C_6$), halogenoalkyl($C_1-C_4$), halogenoalkyl($C_1-C_4$)thio, halogenoalkoxy($C_1-C_4$), dialkyl($C_1-C_4$)amino or dihalogenoamino, $R^2$ represents hydrogen, alkyl($C_1-C_6$), cycloalkyl($C_3-C_7$) which is optionally substituted by halogen or halogenoalkyl($C_1-C_4$); or halogenoalkyl($C_1-C_4$)thio, alkoxy($C_1-C_6$)carbonyl or trialkyl($C_1-C_6$)silyl, $R^3$ represents hydrogen or alkyl($C_1-C_6$), $R^4$ represents hydrogen or alkyl($C_1-C_6$), $R^5$ represents hydrogen, alkyl($C_1-C_6$), phenyl or alkyl($C_1-C_4$)thio, $R^6$ represents alkyl($C_1-C_6$) which is optionally substituted by halogen, halogenoalkyl($C_1-C_4$) or halogenoalkoxy($C_1-C_4$), or represents cycloalkyl($C_3-C_7$) which is optionally substituted by halogen, halogenoalkyl($C_1-C_4$) halogenoalkoxy($C_1-C_4$), or represents the radical

where $R^7$ and $R^8$ can be identical or different and represent hydrogen, halogen, alkyl($C_1-C_6$), nitro, cyano, halogenoalkyl($C_1-C_6$), alkoxy($C_1-C_6$), halogenoalkoxy($C_1-C_6$), alkyl($C_1-C_6$)thio, halogenoalkyl ($C_1-C_6$)thio, phenoxy or phenylthio each of which is optionally substituted by halogen, halogenoalkyl($C_1-C_6$), alkoxy($C_1-C_6$) or alkyl($C_1-C_6$), or represent mono- or dialkylamino each of which has 1 to 6 carbon atoms in the alkyl radical and each of which is optionally substituted by halogen, alkoxy($C_1-C_4$) or halogenoalkyl($C_1-C_4$), or represent cycloalkyl($C_3-C_7$) which is optionally substituted by alkyl($C_1-C_4$), alkoxy($C_1-C_4$), halogen or alkyl($C_1-C_4$)thio, or represent alkoxy($C_1-C_6$)carbonyl, alkenyl($C_2-C_6$)oxy, alkinyl($C_2-C_6$), alkyl($C_1-C_4$)thionyl, alkyl($C_1-C_4$)sulphonyl, halogenoalkyl($C_1-C_4$)thionyl, halogenoalkyl($C_1-C_4$)sulphonyl or halogenoalkoxy($C_1-C_4$)-carbonyl, or where $R^7$ and $R^8$ together represent one of the following bivalent radicals:

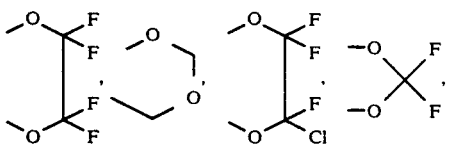

X represents oxygen or sulphur and Y and Z can be identical or different and represent hydrogen, alkyl($C_1-C_6$), halogen, halogenoalkyl($C_1-C_6$), alkoxy($C_1-C_6$), alkyl($C_1-C_6$)thio, halogenoalkoxy($C_1-C_4$), halogenoalkyl($C_1-C_4$)thio, alkoxy($C_1-C_4$)carbonyl, halogenoalkoxy($C_1-C_4$)-carbonyl, phenoxy or phenylthio each of which is optionally substituted by halogen, alkyl($C_1-C_4$), alkoxy($C_1-C_4$) or halogenoalkyl($C_1$–$C_4$), or represent alkenyl($C_2$–$C_6$)oxy, alkinyl($C_2$–$C_6$), alkyl($C_1$–$C_4$)-thionyl, alkyl($C_1$–$C_4$)sulphonyl, halogenoalkyl($C_1$–$C_4$)thionyl, halogenoalkyl($C_1$–$C_4$)sulphonyl, mono- or dialkyl($C_1$–$C_6$)amino each of which is optionally substituted by halogen, alkoxy($C_1$–$C_4$), halogenoalkyl($C_1$–$C_4$); or represent nitro or cyano, or where Y and Z together represent optionally fluorine-and/or chlorine-substituted 3,4-methylenedioxy or 3,4-ethylenedioxy.

Particularly preferred compound of the formula (I) are those in which $R^1$ represents a 1H-pyrrol-1-yl, 1H-pyrazol-1-yl, 1H-imidazol-1-yl, 2H-1,2,3-triazol-2-yl, 1H-1,2,3-triazol-1-yl, 1H-1,2,4-triazolyl-(1), 4H-1,2,4-triazolyl-(4)-, 2H-tetrazol2-yl, 1H-tetrazol-1-yl, radical, each of which is optionally substituted by fluorine, chlorine, bromine, iodine, alkyl($C_1$–$C_4$), CN, $NO_2$, alkoxy($C_1$–$C_4$)carbonyl, alkyl($C_1$–$C_3$)thio, alkoxy($C_1$–$C_4$), halogenoalkyl($C_1$–$C_3$ or halogenoalkyl-($C_1$–$C_3$)thio or halogenoalkoxy($C_1$–$C_4$)carbonyl, $R^2$ represents hydrogen, alkyl($C_1$–$C_4$), optionally fluorine-, chlorine-, bromine- or halogenoalkyl($C_1$–$C_3$)-substituted cycloalkyl($C_3$–$C_6$), halogenoalkyl($C_1$–$C_3$), halogenoalkyl($C_1$–$C_3$)thio alkoxy($C_1$–$C_4$)carbonyl or trialkyl($C_1$–$C_4$)silyl, $R^3$ represents hydrogen or alkyl($C_1$–$C_4$), $R^4$ represents hydrogen or alkyl($C_1$–$C_4$), $R^5$ represents hydrogen, alkyl($C_1$–$C_4$), phenyl or alkyl($C_1$–$C_3$)thio, $R^6$ represents alkyl($C_1$–$C_4$) which is optionally substituted by fluorine, chlorine, bromine, halogenoalkyl($C_1$–$C_3$) or halogenoalkoxy($C_1$–$C_3$), or represents cycloalkyl($C_3$–$C_6$) which is optionally substituted by fluorine, chlorine, bromine, halogenoalkyl($C_1$–$C_3$) or halogenoalkoxy($C_1$–$C_3$), or represents the radical

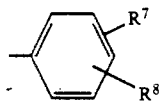

where $R^7$ and $R^8$ can be identical or different and represent hydrogen, fluorine, chlorine, bromine, iodine, alkyl($C_1$–$C_4$), nitro cyano, halogenoalkyl($C_1$–$C_3$), alkoxy($C_1$–$C_4$), halogenoalkoxy($C_1$–$C_3$), alkyl($C_1$–$C_3$)thio, halogenoalkyl($C_1$–$C_3$)thio, or phenoxy which is optionally substituted by fluorine, chlorine, bromine, halogenoalkyl($C_1$–$C_3$), alkoxy($C_1$–$C_3$) or alkyl($C_1$–$C_3$), or represent mono- or dialkylamino each of which has 1 to 4 carbon atoms in the alkyl radical and each of which is optionally substituted by fluorine, chlorine, bromine, alkoxy($C_1$–$C_3$) or halogenoalkyl($C_1$–$C_3$), or represent cycloalkyl($C_3$–$C_6$) which is optionally substituted by alkyl($C_1$–$C_3$), alkoxy($C_1$–$C_3$), fluorine, chlorine, bromine or alkyl($C_1$–$C_3$)thio, or where $R^7$ and $R^8$ together represent one of the following bivalent radical:

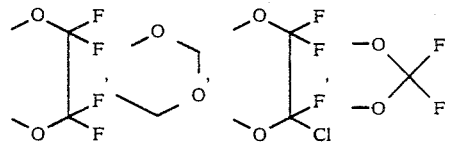

X represents oxygen or sulphur and Y and Z can be identical or different and represent hydrogen, alkyl($C_1$–$C_4$), fluorine, chlorine, bromine, iodine, halogenoalkyl($C_1$–$C_4$), alkoxy($C_1$–$C_4$), alkyl($C_1$–$C_4$)thio, halogenoalkoxy($C_1$–$C_3$), halogenoalkyl($C_1$–$C_3$)thio, alkoxy($C_1$–$C_3$)carbonyl, phenoxy or phenylthio each of which is optionally substituted by fluorine, chlorine, bromine, alkyl($C_1$–$C_3$), alkoxy($C_1$–$C_3$) or halogenoalkyl($C_1$–$C_3$), or represent halogenoalkoxy($C_1$–$C_3$)carbonyl, alkenyl($C_2$–$C_4$)oxy, alkinyl($C_2$–$C_4$), alkyl($C_1$–$C_3$)thionyl, alkyl($C_1$–$C_3$)sulphonyl, halogenoalkyl($C_1$–$C_3$)thionyl, halogenoalkyl($C_1$–$C_3$)sulphonyl, nitro or cyano, or where Y and Z together represent optionally fluorine-and/or chlorine-substituted 3,4-methylenedioxy or 3,4-ethylenedioxy.

The meaning of halogenoalkyl in the substituents in the radicals halogenoalkyl, halogenoalkoxy, halogenoalkylthio, halogenoalkylthionyl and halogenoalkylsulphonyl contains preferably 1 to 4, in particular 1 or 2, carbon atoms and preferably 1 to 5, in particular 1 to 3, identical or different halogen atoms, preferred halogen atoms being fluorine, chlorine and bromine, especially fluorine and chlorine. Examples which may be mentioned are trifluoromethyl, chlorodifluoromethyl, bromomethyl, 2,2,2-trifluoroethyl and pentafluoroethyl.

The following substituted pyrazoline derivatives of the general formula (I) may be mentioned individually in addition to the compounds mentioned in the Preparation Examples:

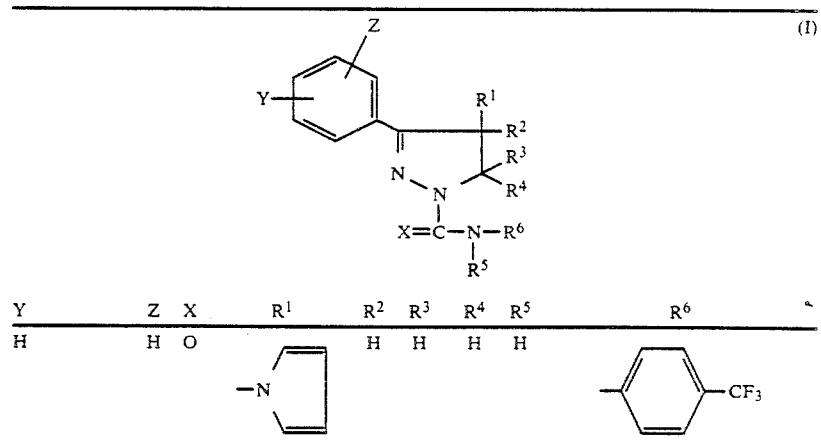

-continued $$\text{(I)}$$

| Y | Z | X | R¹ | R² | R³ | R⁴ | R⁵ | R⁶ |
|---|---|---|---|---|---|---|---|---|
| H | H | O | -N(pyrrolyl) | H | H | H | H | 4-OCF₃-C₆H₄ |
| 4-CF₃ | H | O | -N(pyrrolyl) | H | H | H | H | 4-CF₃-C₆H₄ |
| 4-CF₃ | H | O | -N(pyrrolyl) | H | H | H | H | 4-Cl-C₆H₄ |
| 4-CF₃ | H | O | -N(pyrrolyl) | H | H | H | H | 4-OCF₃-C₆H₄ |
| 4-Br | H | O | -N(pyrrolyl) | H | H | H | H | 4-CF₃-C₆H₄ |
| 3-CF₃ | H | O | -N(pyrrolyl) | H | H | H | H | 4-Cl-C₆H₄ |
| 3-CF₃ | H | O | -N(pyrrolyl) | H | H | H | H | 4-OCHF₂-C₆H₄ |
| 4-F | H | O | -N(pyrrolyl) | H | H | H | H | 4-Cl-C₆H₄ |
| 4-F | H | O | -N(pyrrolyl) | H | H | H | H | 4-CF₃-C₆H₄ |
| 4-F | H | O | -N(pyrrolyl) | H | H | H | H | 4-OCF₃-C₆H₄ |
| 4-F | H | O | -N(pyrrolyl) | H | H | H | H | 4-OCHF₂-C₆H₄ |

-continued $$(I)$$

[Structure: Phenyl ring with Y and Z substituents, connected via C=N to a pyrazoline ring bearing R¹, R², R³, R⁴ substituents; N-C(=X)-N(R⁵)(R⁶) group]

| Y | Z | X | R¹ | R² | R³ | R⁴ | R⁵ | R⁶ |
|---|---|---|---|---|---|---|---|---|
| 4-F | H | O | –N(pyrrolyl) | H | H | H | H | –C₆H₄–SCF₃ (4-) |
| 4-F | H | O | –N(pyrrolyl) | H | H | H | H | –C₆H₄–OCF₂–CHF₂ (4-) |
| 4-F | H | O | –N(pyrrolyl) | H | H | H | H | –C₆H₄–CHF₂ (4-) |
| 4-F | H | O | –N(pyrrolyl) | H | H | H | H | –C₆H₄–F (4-) |
| 4-Cl | H | O | –N(pyrrolyl) | H | H | H | H | –C₆H₄–CF₃ (4-) |
| 4-OCHF₂ | H | O | –N(pyrrolyl) | H | H | H | H | –C₆H₄–OCF₃ (4-) |
| 4-F | H | O | –N(imidazolyl) | H | H | H | H | –C₆H₄–CF₃ (4-) |
| 4-F | H | O | –N(imidazolyl) | H | H | H | H | –C₆H₄–Cl (4-) |
| 4-F | H | O | –N(imidazolyl) | H | H | H | H | –C₆H₄–OCF₃ (4-) |
| 4-F | H | O | –N(imidazolyl) | H | H | H | H | –C₆H₄–SCF₃ (4-) |
| 4-F | H | O | –N(imidazolyl) | H | H | H | H | –C₆H₄–OCHF₂ (4-) |

Note: R¹ groups shown are N-linked pyrrolyl (first 6 rows) and N-linked imidazolyl (last 5 rows); R⁶ groups are para-substituted phenyl rings as indicated.

-continued

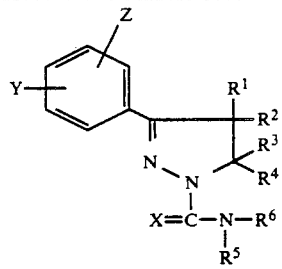

| Y | Z | X | R¹ | R² | R³ | R⁴ | R⁵ | R⁶ |
|---|---|---|---|---|---|---|---|---|
| 4-Cl | H | O | pyrazol-1-yl | H | H | H | H | 4-CF₃-phenyl |
| 4-Cl | H | O | pyrazol-1-yl | H | H | H | H | 4-OCF₃-phenyl |
| 4-Cl | H | O | pyrazol-1-yl | H | H | H | H | 4-OCHF₂-phenyl |
| 4-Cl | H | O | pyrazol-1-yl | H | H | H | H | 3,4-(OCF₂CF₂O)-phenyl |
| 4-OCHF₂ | H | O | pyrazol-1-yl | H | H | H | H | 4-CF₃-phenyl |
| 4-OCHF₂ | H | O | pyrazol-1-yl | H | H | H | H | 4-OCF₃-phenyl |
| 4-OCHF₂ | H | O | pyrazol-1-yl | H | H | H | H | 4-Cl-phenyl |
| 4-OCHF₂ | H | O | pyrazol-1-yl | H | H | H | H | 4-OCF₂—CHF₂-phenyl |
| 4-OCH₂CF₃ | H | O | 4-Cl-pyrazol-1-yl | H | H | H | H | 4-CF₃-phenyl |
| 4-OCH₂CF₃ | H | O | 4-Cl-pyrazol-1-yl | H | H | H | H | 4-Cl-phenyl |

-continued $$\text{(I)}$$

Structure: Aryl group (with Y and Z substituents) connected via C=N to a pyrazoline ring bearing R¹, R², R³, R⁴ substituents, with N-N-C(=X)-N(R⁵)(R⁶) side chain.

| Y | Z | X | R¹ | R² | R³ | R⁴ | R⁵ | R⁶ |
|---|---|---|---|---|---|---|---|---|
| 4-CF₃ | H | O | pyrazol-1-yl (4-Cl) | H | H | H | H | 4-CF₃-phenyl |
| 4-CF₃ | H | O | pyrazol-1-yl (4-Cl) | H | H | H | H | 4-OCF₃-phenyl |
| H | H | O | 1,2,4-triazol-1-yl | H | H | H | H | 4-CF₃-phenyl |
| 4-t.-Butyl | H | O | 1,2,4-triazol-1-yl | H | H | H | H | 4-CF₃-phenyl |
| 3-CF₃ | H | O | 1,2,4-triazol-1-yl | H | H | H | H | 4-OCF₃-phenyl |
| 4-CH₃ | H | O | 1,2,4-triazol-1-yl | H | H | H | H | 4-CF₃-phenyl |
| 4-CH₃ | H | O | 1,2,4-triazol-1-yl | H | H | H | H | 4-Cl-phenyl |
| 4-Cl | H | O | 1,2,4-triazol-1-yl (isomer) | H | H | H | H | 4-CF₃-phenyl |
| 4-Cl | H | O | 1,2,3,4-tetrazol-2-yl | H | H | H | H | 4-CF₃-phenyl |
| 4-F | H | O | 1,2,3,4-tetrazol-2-yl | H | H | H | H | 4-OCF₃-phenyl |

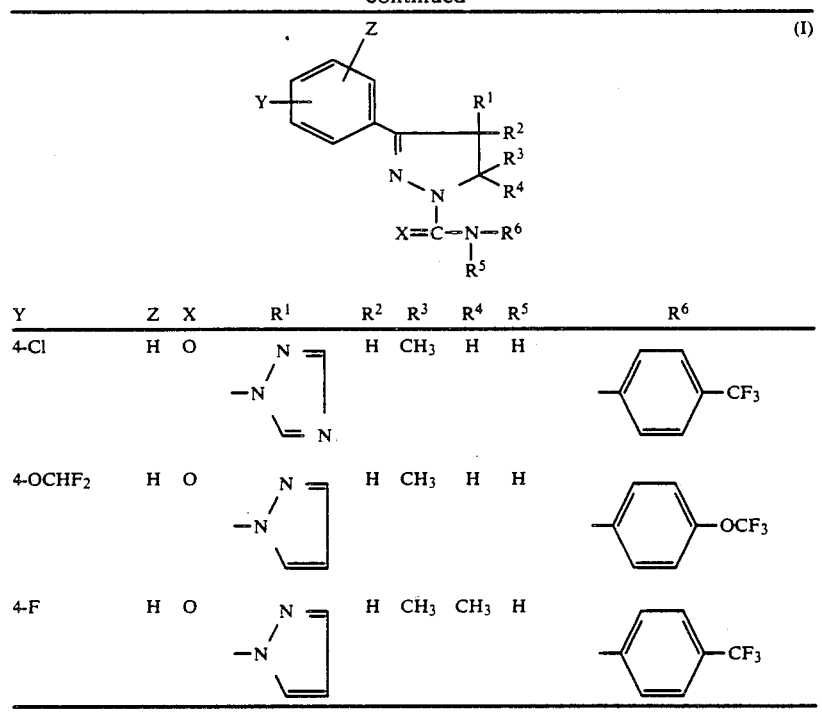

| Y | Z | X | R¹ | R² | R³ | R⁴ | R⁵ | R⁶ |
|---|---|---|---|---|---|---|---|---|
| 4-Cl | H | O | (pyrazol-triazole) | H | CH₃ | H | H | -C₆H₄-CF₃ |
| 4-OCHF₂ | H | O | (pyrazolyl) | H | CH₃ | H | H | -C₆H₄-OCF₃ |
| 4-F | H | O | (pyrazolyl) | H | CH₃ | CH₃ | H | -C₆H₄-CF₃ |

If, for example,
3-(4'-fluorophenyl)-4-(1"H-4"-chloropyrazol-1"-yl)-4,5-dihydropyrazole and 4-difluoromethoxyphenyl isocyanate are used as starting substances, the course of the reaction of process a) according to the invention can be represented by the following equation:

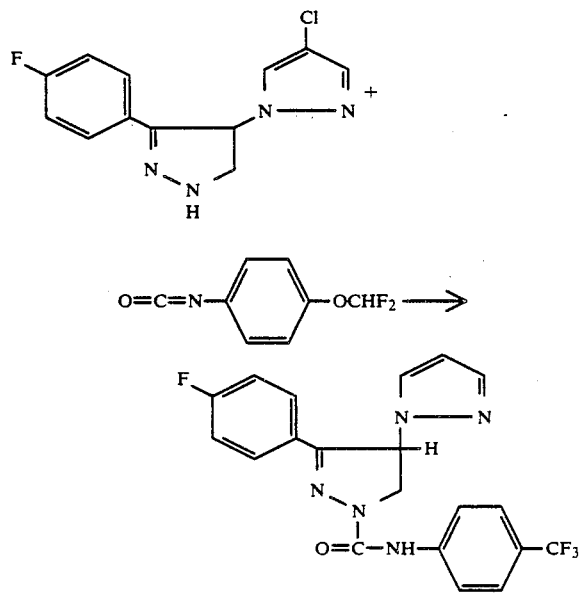

If, for example,
4-trifluoromethyl-anilide of 3-(4-fluorophenyl)-4-(1H-pyrazol-1-yl)-4,5-dihydro-1-pyrazolecarboxylic acid and 2-iodopropane are used as starting substances, the course of the reaction of process b) according to the invention can be represented as follows:

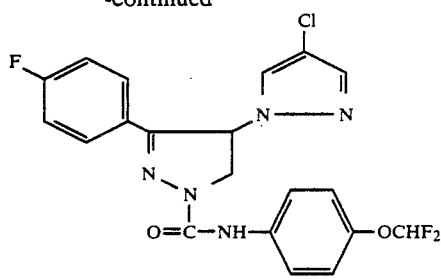

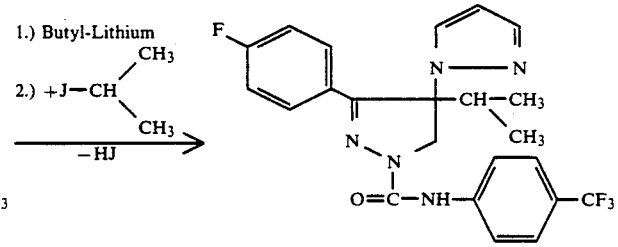

Formula (II) provides a general definition of the pyrazoline derivatives required as starting substances for carrying out process (a) according to the invention. In this formula (II), R¹, R², R³, R⁴, Y and Z preferably represent those radicals which have already been mentioned in connection with the description of the substances of the formula (I) according to the invention as being preferred for these substituents. The pyrazoline derivatives of the formula (II) are new.

They are prepared by reacting compounds of the formula (VI)

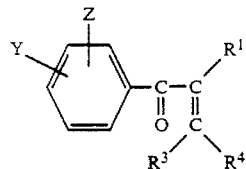
(VI)

with hydrazine hydrate in a polar organic solvent, preferably an alkanol, at temperatures of from 20° to 80° C., in particular at 30° to 60° C.:

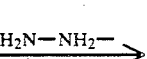
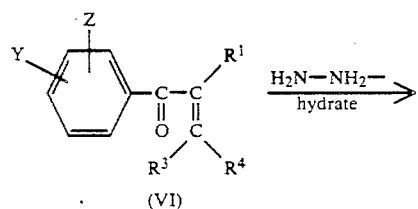
(II)

Depending on the meaning of the substituents $R^3$ and $R^4$, the following preparation variants of the starting compounds of the formula (VI) are the result

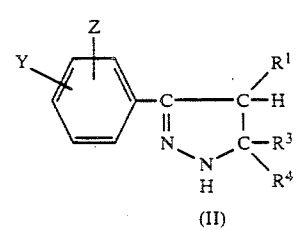
(VI)

a) $R^3$ and $R^4$ in the formula (VI) represent hydrogen

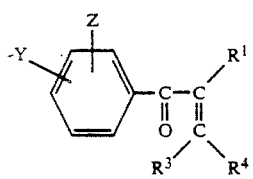
(VIa)

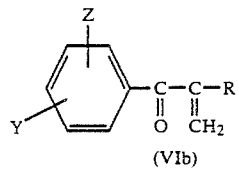
(VIb)

In this case, the compound is reacted with a formalin solution in a polar organic solvent, preferably an alkanol and in particular in ethanol or methanol, with the addition of small amounts of an organic base, in particular of piperidine, and with the addition of glacial acetic acid.

b) $R^3$ in the formula (VI) represents alkyl or aryl, and $R^4$ represents hydrogen:

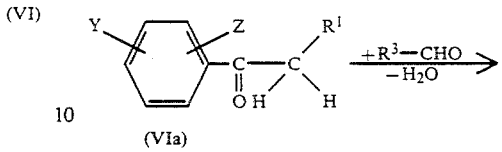
(VIa)

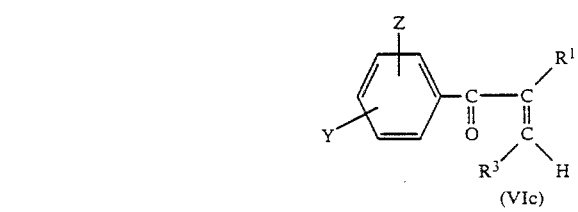
(VIc)

The process conditions correspond to those of the reaction with formaldehyde.

c) $R^3$ and $R^4$ in the formula represent alkyl:

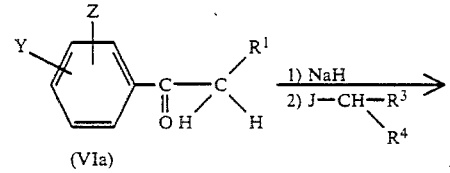
(VIa)

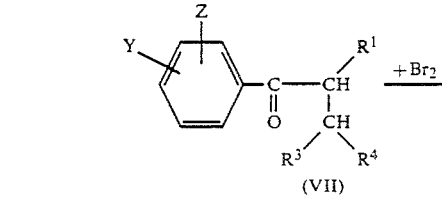
(VII)

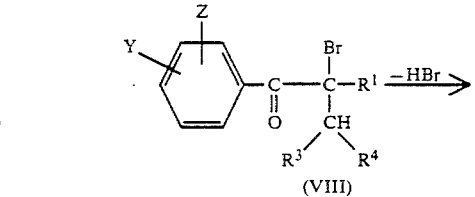
(VIII)

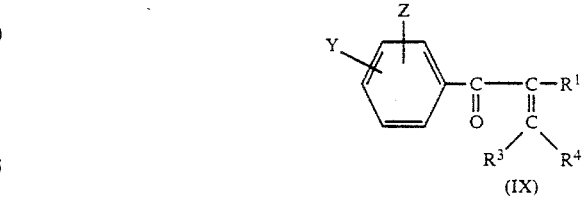
(IX)

In this case, compound (VI) is first converted into the salt with the aid of a strong base, and this is then reacted with a halide, in particular an iodide of the formula

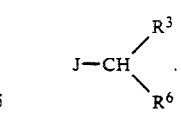

The compound of the formula (VII) which is formed in this process is brominated, and the intermediate of the formula (IX) is subsequently prepared by adding a base with the elimination of HBr.

Compounds of formula (II) in which $R^3$ and $R^4$ stand for hydrogen can be produced alternatively by reacting compounds of formula XII with hydrazine-hydrate in a polar solvent, preferably in an alkanol at temperatures between 0° C. and 60° C.:

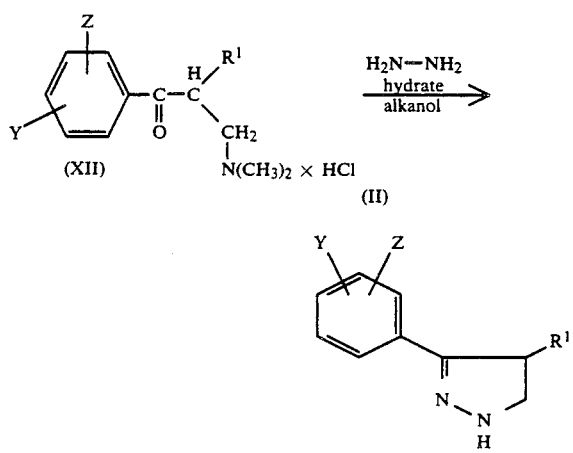

Compounds of formula (XII) can be produced by reacting compounds of formula VIa with dimethylaminohydrochloride and paraformaldehyde in an alkanol at temperatures between 30° and 80° C. and subsequent precipitation of the salt with an non-polar solvent such as an ether:

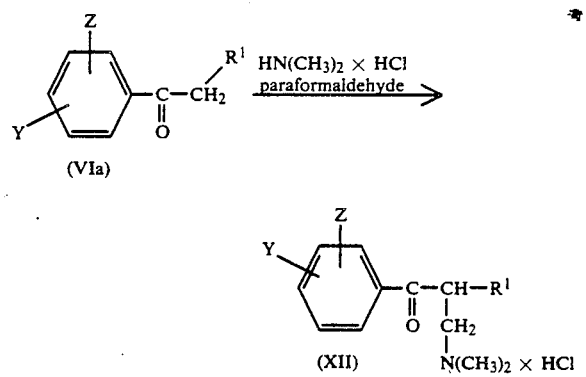

Some of the compounds of the formula (VIa) are new. They are prepared by reacting the compounds

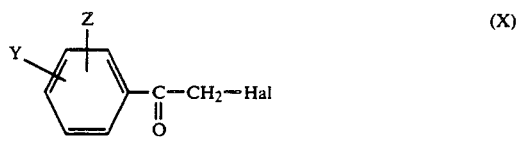

where Y and Z have the abovementioned meaning and Hal represents halogen
with the compounds $R^1$—H, with the aid of an organic or inorganic base and with the elimination of hydrogen halide. The compounds of the formula (X) are known substances.

In process variant b), compounds of the formula (IV)

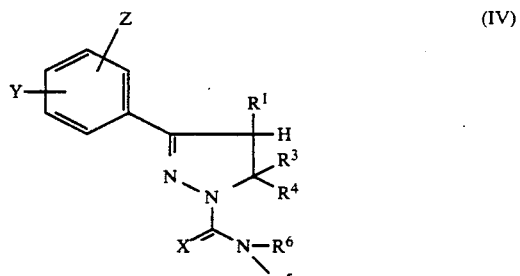

in which X, Y, Z, $R^1$, $R^3$, $R^4$, $R^5$ and $R^6$ have the abovementioned meaning, are reacted with a strong base, preferably an organometallic compound, in particular with butyl-lithium, in inert organic solvent at temperatures of from $-50°$ to $0°$ C., in particular of from $-30°$ C. to $-15°$ C., if appropriate in the presence of a protective gas atmosphere, in particular rare-gas atmosphere such as, for example, argon, and the product is subsequently reacted with a halide Hal—$R^2$ where $R^2$ represents alkyl, optionally substituted cycloalkyl, halogenoalkyl, alkoxycarbonyl or halogenoalkylthio,
at $0°$ to $60°$ C., in particular at $-10°$ to $-40°$ C., and the product is worked up in the customary manner by adding water and extracting the mixture with ether.

This gives compounds of the formula (XI)

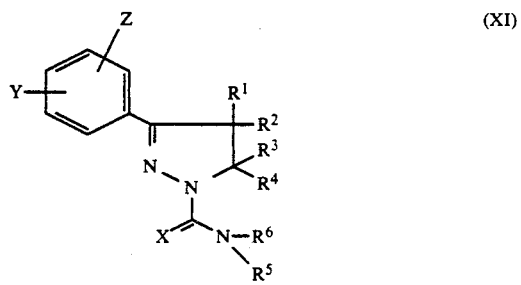

where X, Y, Z, $R^1$, $R^2$, $R^3$, $R^4$, $R^5$, $R^6$ and $R^9$ have the abovementioned meanings.

The active compounds are suitable for combating animal pests, especially arthropods and nematodes, in particular insects and arachnids, encountered in agriculture, in animal husbandry, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, *Reticulitermes* spp. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varive stis*, Atomaria spp., *Oryzaephilus surinamensis*, Antho nomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Cono derus spp., *Melolontha melolontha, Amphimallon solsti tialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Hydrotaea spp., Haematobia spp., Glossina spp., Melophagus spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*. From the order of the Siphonaptera, for example, Xenopsylla cheopis Ceratophyllus spp. and Ctenocephalides spp. From the order of the Arachnida, for example, *Scorpio maurus* and *Latrodectus mactans*. From the order of the Acarina, for example, *Acarum siro*, Argas spp., Ornithodoros spp., *Dermanyssus gallinae*, Ornithonyssus spp., *Eriophyes ribis, Phyllocoptruta oleivora*, Boophilus spp., Rhipicephalus spp., Amblyomma spp., Hyalomma spp., Ixodes spp., Dermacentor spp., Haemaphysalis spp., Otobius spp., Psoroptes spp., Chorioptes spp., Sarcoptes spp., Psorergates spp., Demodex spp., Notoedres spp., Tarsonemus spp., *Bryobia praetiosa*, Panonychus spp. and Tetranychus spp.

The active compounds according to the invention are not only active against plant, hygiene and stored-product pests, but also, in the veterinary medicine sector, against animal parasites (ectoparasites and endoparasites), such as scaly ticks, argasidae, scab mites, trombidae, flies (piercing and sucking), parasitic fly larvae, lice, hair lice, bird lice, fleas and worms which live as endoparasites.

They are active against normally sensitive and resistant species and strains, as well as against all parasitic and non-parasitic stages of development of the ecto- and endoparasites.

The active compounds according to the invention have a strong insecticidal and acaricidal activity.

They can be employed particularly successfully against insects which are harmful to plants, such as, for example, against the green peach aphid (*Myzus persicae*), or against the larvae of the mustard beetle (*Phaedon cochleariae*) or against the larvae of the cabbage moth (*Plutella xylostella*), or against the larvae of the green rice leafhopper (*Nephotettix cincticeps*), or against the larvae of the cotton boll worm (*Heliothis armigera*), or against the larvae of the army worm (*Spodoptera frugiperda*); for combating mites which damage plants, such as, for example, against the common spider mite or the two-spotted spider mite (*Tetranychus urticae*).

In addition, they can be employed with particularly good success for combating pests which live as parasites on warm-blooded animals, such as, for example, against the larvae of the sheep maggot fly (*Lucilia cuprina*), against ticks of cattle (*Boophilus microplus*) or against scab mites (*Psoroptes ovis*), and also against cockroaches (*Blattella germanica* and the like).

Furthermore, the compounds according to the invention also have an activity against parasitic protozoa, and in particular against Coccidia and/or Plasmodium.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphoric esters, carbamates, carboxylic esters, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as by a good stability to alkali on limed substrates.

The active compounds according to the invention are also suitable for combating insects, mites, ticks etc. in the sectors of animal husbandry and cattle breeding; better results, for example higher milk production, greater weight, more attractive animal pelt, longer life etc., can be achieved by combating the pests.

The application of the active compounds according to the invention is effected in this sector in a known fashion, such as by external application in the form of, for example, dipping, spraying, pouring-on, spotting-on and dusting, as well as by means of parenteral application in the form, for example, of an injection, and, furthermore, by means of the feed-through process. In addition, application as moulded articles (collar, ear tag) and application in the form of the so-called environment treatment are also possible.

The biological activity of the compounds according to the invention will be illustrated with the aid of the following examples.

EXAMPLES

Preparation Examples

EXAMPLE 1

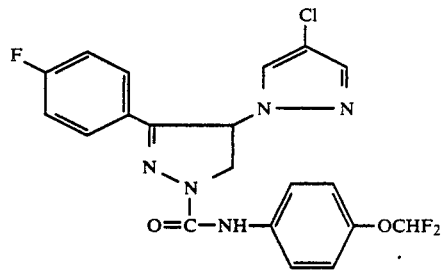

2.64 g (0.01 mol) of 3-(4'-fluorophenyl)-4-(1"H-4"-chloropyrazol-1"-yl)-4,5-dihydropyrazole are dissolved at room temperature in 20 ml of anhydrous acetonitrile, and 2 g of 4-difluoromethoxyphenyl isocyanate are added with stirring. The mixture is heated to 50° C., and 2 to 3 drops of triethylamine are then added. The mixture is subsequently stirred at 50° C. for 1 hours. After the mixture has cooled, the solvent is distilled off in vacuo, and 25 ml of ether are added to the residue. The crystals which separate out after some time are filtered off with suction. 3.1 g of the (4-difluoromethoxy-anilide of 3(4'-fluorophenyl)-4-(1"H-4"chloropyrazol-1"-yl)-4,5-dihydro-1-pyrazolecarboxylic acid of melting point 200° C. are obtained.

The following can be prepared in an analogous manner:

General formula

-continued

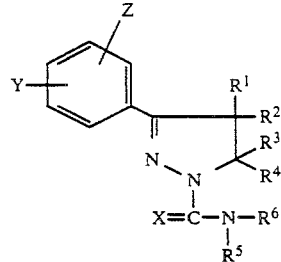

(I)

| Ex. No. | Y | Z | X | R¹ | R² | R³ | R⁴ | R⁵ | R⁶ | M.p. |
|---|---|---|---|---|---|---|---|---|---|---|
| 2 | 4-F | H | O | -N(N=CH-N=CH-) (1,2,4-triazol-1-yl) | H | H | H | H | 4-CF₃-cyclohexyl | oil |
| 3 | 4-Cl | H | O | 1,2,4-triazol-1-yl | H | H | H | H | 3-CF₃-cyclohexyl | oil |
| 4 | 4-Cl | H | O | 1,2,4-triazol-1-yl | H | H | H | H | 4-CF₃-cyclohexyl | oil |
| 5 | 4-Cl | H | O | 1,2,4-triazol-1-yl | H | H | H | H | cyclohexyl | 149° C. |
| 6 | 4-F | H | O | 1,2,4-triazol-1-yl | H | H | H | H | cyclohexyl | Oel |
| 7 | 4-Cl | H | O | pyrazol-1-yl | H | H | H | H | cyclohexyl | 195–196° C. |
| 8 | 4-Cl | H | O | pyrazol-1-yl | H | H | H | H | 3-CF₃-cyclohexyl | Oel |
| 9 | 4-Cl | H | O | 4-Cl-pyrazol-1-yl | H | H | H | H | 4-CF₃-cyclohexyl | 222° C. |
| 10 | 4-Cl | H | O | pyrazol-1-yl | H | H | H | H | 4-CF₃-cyclohexyl | Oel |
| 11 | 4-Cl | H | O | 3,5-dimethyl-pyrazol-1-yl | H | H | H | H | 4-CF₃-cyclohexyl | 176° C. |

-continued

| # | R | | X | Het | | | | | Ar | mp |
|---|---|---|---|---|---|---|---|---|---|---|
| 12 | 4-F | H | O | N=N−N(CH₃)=C−CH₃ pyrazole with 3,5-diCH₃ | H | H | H | H | cyclohexyl-H, CF₃ | oil |
| 13 | 4-CF | H | S | pyrazole-Cl | H | H | H | H | cyclohexyl-H, CF₃ | oil |
| 14 | 4-Cl | H | S | pyrazole | H | H | H | H | cyclohexyl-H, CF₃ | oil |
| 15 | 4-Cl | H | S | 1,2,4-triazole | H | H | H | H | cyclohexyl-H, CF₃ | oil |
| 16 | 4-OCHF₂ | H | O | 1,2,4-triazole | H | H | H | H | cyclohexyl-H, CF₃ | oil |
| 17 | 4-OCHF₂ | H | O | pyrazole | H | H | H | H | cyclohexyl-H, CF₃ | oil |
| 17a | 4-F | H | O | pyrazole-Cl | H | H | H | H | phenyl-CF₃ | |
| 18 | 4-OCHF₂ | H | O | pyrazole-Cl | H | H | H | H | cyclohexyl-H, CF₃ | |
| 19 | 4-OCHF₂ | H | S | pyrazole | H | H | H | H | cyclohexyl-H, CF₃ | |
| 20 | 4-OCHF₂ | H | O | pyrazole | H | H | H | H | phenyl-OCF₃ | 170–180° C. |
| 21 | 4-Cl | H | O | pyrazole | H | H | H | H | phenyl-Cl | <250° C. |
| 22 | 4-Cl | H | O | pyrazole | H | H | H | H | phenyl-CF₃ | 225° C. |

| | | | | | | | | | |
|---|---|---|---|---|---|---|---|---|---|
| 23 | 4-Cl | H | O | -N(pyrazole) | H | H | H | H | 4-OCF₃-phenyl | 229° C. |
| 24 | 4-Cl | H | O | -N(pyrazole) | H | H | H | H | 4-SCF₃-phenyl | 233° C. |
| 25 | 4-Cl | H | O | -N(pyrazole) | H | H | H | H | 4-(4-CF₃-phenoxy)-phenyl | 236–237° C. |
| 26 | 4-Cl | H | O | -N(pyrazole) | H | H | H | H | 4-F-phenyl | 185° C. |
| 27 | 4-Cl | H | O | -N(pyrazole) | H | H | H | H | 4-OCHF₂-phenyl | 224° C. |
| 28 | 4-Cl | H | O | -N(pyrazole) | H | H | H | H | 4-OCF₂-CHF₂-phenyl | 225° C. |
| 29 | 4-Cl | H | O | -N(pyrazole) | H | H | H | H | 2-(OCF₂CF₃)-phenyl | 227° C. |
| 30 | 4-Cl | H | O | -N(pyrazole) | H | H | H | H | 4-NO₂-phenyl | <250° C. |
| 31 | 4-Cl | H | O | -N(pyrazole) | H | H | H | H | 4-CH₃-phenyl | 235° C. |
| 32 | 4-Cl | H | O | -N(pyrazole) | H | H | H | H | 4-OCH₃-phenyl | 245° C. |
| 33 | 4-Cl | H | O | -N(pyrazole) | H | H | H | H | 4-OC₂H₅-phenyl | 215° C. |
| 34 | 4-Cl | H | O | -N(pyrazole) | H | H | H | H | 3,4-(methylenedioxy)-phenyl | 170° C. |

-continued

| | | | | | | | | |
|---|---|---|---|---|---|---|---|---|
| 35 | 4-OCHF$_2$ | H | O | -N-N=CH-CH= (pyrazole) | H H H H | 4-Cl-phenyl | | 170° C. |
| 36 | 4-OCHF$_2$ | H | O | pyrazole | H H H H | 4-CF$_3$-phenyl | | 175° C. |
| 37 | 4-OCHF$_2$ | H | O | pyrazole | H H H H | 2-(OCF$_2$CFClH... )-phenyl | | resin |
| 38 | 4-OCHF$_2$ | H | O | pyrazole | H H H H | 4-F-phenyl | | 195° C. |
| 39 | 4-OCHF$_2$ | H | O | pyrazole | H H H H | 4-SCF$_3$-phenyl | | 219° C. |
| 40 | 4-OCHF$_2$ | H | O | pyrazole | H H H H | 4-NO$_2$-phenyl | | <230° C. |
| 41 | 4-OCHF$_2$ | H | O | pyrazole | H H H H | 4-OCHF$_2$-phenyl | | resin |
| 42 | 4-F | H | O | 5-Cl-pyrazole | H H H H | 4-CF$_3$-phenyl | | 211° C. |
| 43 | 4-F | H | O | 5-Cl-pyrazole | H H H H | 4-OCF$_3$-phenyl | | 227° C. |
| 44 | 4-Cl | H | O | 5-Cl-pyrazole | H H H H | 4-Cl-phenyl | | 216° C. |
| 45 | 4-Cl | H | O | 5-Cl-pyrazole | H H H H | 4-CF$_3$-phenyl | | 213° C. |

-continued

| | | | | | | | | |
|---|---|---|---|---|---|---|---|---|
| 46 | 4-Cl | H | O | -N(N=CH-CCl=) (chloropyrazole) | H H H H | | 4-OCF₃-phenyl | 217° C. |
| 47 | 4-Cl | H | O | -N(N=CH-CCl=) | H H H H | | 4-NO₂-phenyl | <250° C. |
| 48 | 4-F | H | O | -N(N=CH-CCl=) | H H H H | | 4-NO₂-phenyl | <250° C. |
| 49 | 4-F | H | O | -N(N=CH-CCl=) | H H H H | | 3,4-(OCF₂-CHF₂ bridged dioxy)-phenyl | |
| 50 | 4-F | H | O | -N(N=CH-CCl=) | H H H H | | 4-CH₃-phenyl | 235° C. |
| 51 | 4-F | H | O | -N(N=CH-CCl=) | H H H H | | 4-OCH₃-phenyl | 195° C. |
| 52 | 4-F | H | O | -N(N=CH-CCl=) | H H H H | | 4-OC₂H₅-phenyl | 196° C. |
| 53 | 4-F | H | O | -N(N=CH-CCl=) | H H H H | | 4-OCF₂-CHF₂-phenyl | 209° C. |
| 54 | 4-Cl | H | O | -N(N=CH-CCl=) | H H H H | | 4-OCHF₂-phenyl | 179° C. |
| 55 | 4-Cl | H | O | -N(N=CH-CCl=) | H H H H | | 4-(O-CF₂-CHF-CF₃)-phenyl | 186° C. |

| | | | | | | | | | |
|---|---|---|---|---|---|---|---|---|---|
| 56 | 4-Cl | H | O | 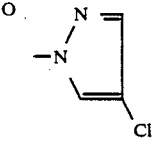 | H | H | H | H | 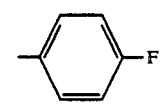 | 194° C. |
| 57 | 4-Cl | H | O | 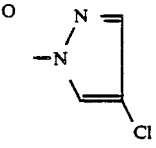 | H | H | H | H | 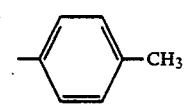 | 245° C. |
| 58 | 4-Cl | H | O | 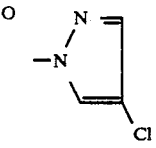 | H | H | H | H | 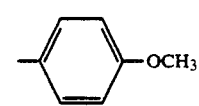 | 222° C. |
| 59 | 4-Cl | H | O | 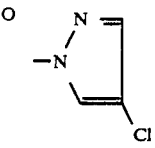 | H | H | H | H | 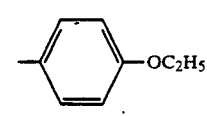 | 241° C. |
| 60 | 4-Cl | H | O | 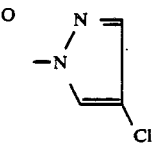 | H | H | H | H | 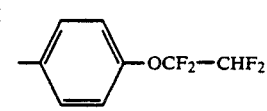 | 239° C. |
| 61 | 4-Cl | H | O | 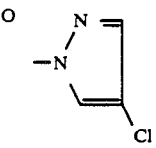 | H | H | H | H | 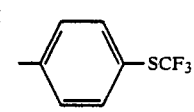 | <250° C. |
| 62 | 4-OCHF$_2$ | H | O | 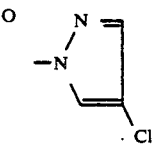 | H | H | H | H | 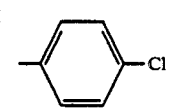 | 207° C. |
| 63 | 4-OCHF$_2$ | H | O | 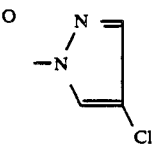 | H | H | H | H | 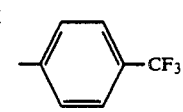 | 192° C. |
| 64 | 4-OCHF$_2$ | H | O | 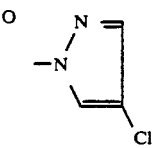 | H | H | H | H | 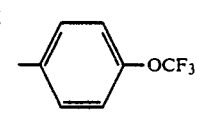 | 170° C. |
| 65 | 4-OCHF$_2$ | H | O | 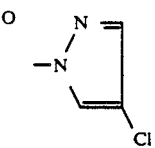 | H | H | H | H | 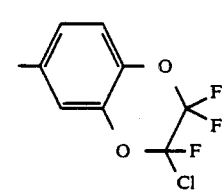 | |

-continued
| | | | | | | | | | |
|---|---|---|---|---|---|---|---|---|---|
| 66 | 4-Cl | H | O | 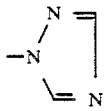 | H | H | H | H | 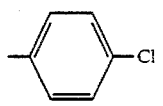 | 230° C. |
| 67 | 4-Cl | H | O | 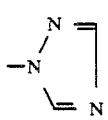 | H | H | H | H | 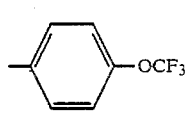 | 198° C. |
| 68 | 4-Cl | H | O | 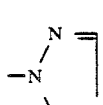 | H | H | H | H | 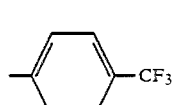 | 228–230° C. |
| 69 | 4-OCHF$_2$ | H | O | 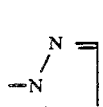 | H | H | H | H | 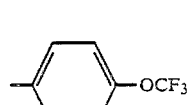 | 215–225° C. |
| 70 | 4-Cl | H | O | 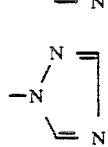 | H | H | H | H | 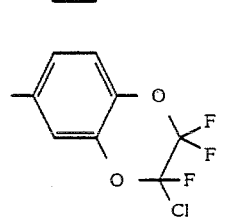 | |
| 71 | 4-Cl | H | O | 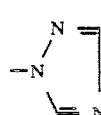 | H | H | H | H | 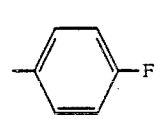 | oil |
| 72 | 4-F | H | O | 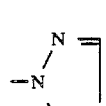 | H | H | H | H | 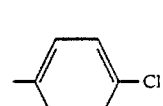 | 191–192° C. |
| 73 | 4-F | H | O | 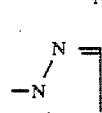 | H | H | H | H | 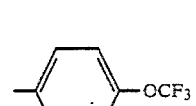 | 215° C. |
| 74 | 4-F | H | O | 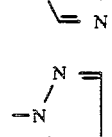 | H | H | H | H | 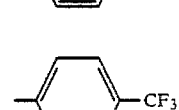 | 217° C. |
| 75 | 4-F | H | O | 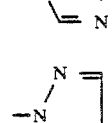 | H | H | H | H | 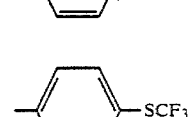 | 246–248° C. |
| 76 | 4-F | H | O | 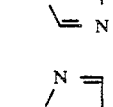 | H | H | H | H | 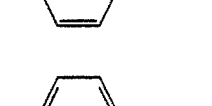 | 212° C. |
| 77 | 4-F | H | O | 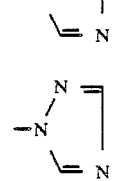 | H | H | H | H | 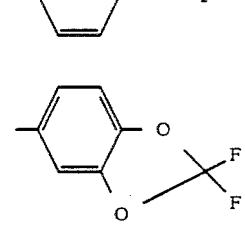 | 226° C. |

-continued

| | | | | | | | | | |
|---|---|---|---|---|---|---|---|---|---|
| 78 | 4-F | H | O | -N(triazole) | H | H | H | H | 2,3-(OCF₂CF₂)-phenyl | 225° C. |
| 79 | 4-F | H | O | -N(triazole) | H | H | H | H | 4-(4-CF₃-phenoxy)-phenyl | 200° C. |
| 80 | 4-Cl | H | O | -N(triazole) | H | H | H | H | 4-SCF₃-phenyl | 235° C. |
| 81 | 4-Cl | H | O | -N(triazole) | H | H | H | H | 4-OCHF₂-phenyl | 231° C. |
| 82 | 4-Cl | H | O | -N(triazole) | H | H | H | H | 2,3-(OCF₂O)-phenyl | 233–234° C. |
| 83 | 4-Cl | H | O | -N(triazole) | H | H | H | H | 4-N(CF₃)₂-phenyl | 227° C. |
| 84 | 4-Cl | H | O | -N(triazole) | H | H | H | H | 3-OCF₃-phenyl | 239–240° C. |
| 85 | 4-Cl | H | O | -N(triazole) | H | H | H | H | 4-(4-CF₃-phenoxy)-phenyl | 214° C. |
| 86 | 4-Cl | H | O | -N(triazole) | H | H | H | H | 3-Cl-4-OCF₃-phenyl | 212° C. |
| 87 | 4-Cl | H | O | -N(triazole) | H | H | H | H | 4-OCF₂-CHF₂-phenyl | 207–208° C. |
| 88 | 4-Cl | H | O | -N(triazole) | H | H | H | H | 4-OCClF₂-phenyl | 212° C. |

| | | | | | | | | | |
|---|---|---|---|---|---|---|---|---|---|
| 89 | 4-Cl | H | O | -N(N=CH-N=CH) triazole | H | H | H | H | 4-(1-methyl-2,2-difluoro-3-chlorocyclobutyl)phenyl | 109° C. |
| 90 | 4-F | H | O | triazole | H | H | H | H | 4-(OCF$_2$—CHF$_2$)phenyl | oil |
| 91 | 4-OCF$_3$ | H | O | triazole | H | H | H | H | 4-Cl-phenyl | 215–218° C. |
| 92 | 4-Cl | H | O | triazole | H | H | H | H | 4-F-phenyl | 135° C. |
| 93 | 4-OCF$_3$ | H | O | triazole | H | H | H | H | 4-CF$_3$-phenyl | 250° C. |
| 94 | 4-OCF$_3$ | H | O | triazole | H | H | H | H | 4-OCF$_3$-phenyl | 230° C. |
| 95 | 4-Cl | H | O | triazole | H | H | H | H | 4-CH$_3$-phenyl | 250° C. |
| 96 | 4-Cl | H | O | triazole | H | H | H | H | 4-OCH$_3$-phenyl | 186° C. |
| 97 | 4-Cl | H | O | triazole | H | H | H | H | 4-OC$_2$H$_5$-phenyl | 210° C. |
| 98 | 4-OCF$_3$ | H | O | triazole | H | H | H | H | 4-SCF$_3$-phenyl | oil |
| 99 | 4-Cl | H | O | triazole | H | H | H | H | 4-NO$_2$-phenyl | <250° C. |
| 100 | 4-Cl | H | O | triazole | H | H | H | H | 3,4-methylenedioxyphenyl | 210° C. |

| | | | | | | | | | |
|---|---|---|---|---|---|---|---|---|---|
| 101 | 4-OCHF$_2$ | H | O | -N(N=CH-N=CH) (1,2,4-triazol-1-yl) | H | H | H | H | 4-Cl-C$_6$H$_4$ | 216° C. |
| 102 | 4-OCHF$_2$ | H | O | 1,2,4-triazol-1-yl | H | H | H | H | 4-CF$_3$-C$_6$H$_4$ | 246° C. |
| 103 | 4-OCHF$_2$ | H | O | 1,2,4-triazol-1-yl | H | H | H | H | 4-SCF$_3$-C$_6$H$_4$ | 231° C. |
| 104 | 4-OCHF$_2$ | H | O | 1,2,4-triazol-1-yl | H | H | H | H | 3,4-(OCF$_2$CHF)-C$_6$H$_3$ (methylenedioxy-type OCF$_2$CHF ring) | 214° C. |
| 105 | 4-Cl | H | O | 3,5-dimethylpyrazol-1-yl | H | H | H | H | 4-OCF$_3$-C$_6$H$_4$ | <250° C. |
| 106 | 4-Cl | H | O | 3,5-dimethylpyrazol-1-yl | H | H | H | H | 4-SCF$_3$-C$_6$H$_4$ | <250° C. |
| 107 | 4-F | H | O | 3,5-dimethylpyrazol-1-yl | H | H | H | H | 4-Cl-C$_6$H$_4$ | 234° C. |
| 108 | 4-F | H | O | 3,5-dimethylpyrazol-1-yl | H | H | H | H | 4-CF$_3$-C$_6$H$_4$ | oil |
| 109 | 4-F | H | O | 3,5-dimethylpyrazol-1-yl | H | H | H | H | 4-F-C$_6$H$_4$ | 240° C. |

-continued

| # | R | | | | | | | | Ar | mp |
|---|---|---|---|---|---|---|---|---|---|---|
| 110 | 4-F | H | O | 3,5-dimethylpyrazol-1-yl | H | H | H | H | 4-OCF₃-C₆H₄ | 250° C. |
| 111 | 4-F | H | O | 3,5-dimethylpyrazol-1-yl | H | H | H | H | 4-SCF₃-C₆H₄ | 260° C. |
| 112 | 4-Cl | H | O | 3,5-dimethylpyrazol-1-yl | H | H | H | H | 4-Cl-C₆H₄ | 245° C. |
| 113 | 4-Cl | H | O | 3,5-dimethylpyrazol-1-yl | H | H | H | H | 4-F-C₆H₄ | 247° C. |
| 114 | 4-Cl | H | O | 3,5-dimethylpyrazol-1-yl | H | H | H | H | 4-CF₃-C₆H₄ | 250° C. |
| 115 | 4-Cl | H | O | 3,5-dimethylpyrazol-1-yl | H | H | H | H | 4-OCH₃-C₆H₄ | 250° C. |
| 116 | 4-Cl | H | O | 3,5-dimethylpyrazol-1-yl | H | H | H | H | 4-CH₃-C₆H₄ | 243° C. |
| 117 | 4-F | H | O | 3,5-dimethylpyrazol-1-yl | H | H | H | H | 4-OCHF₂-C₆H₄ | <250° C. |
| 118 | 4-F | H | O | 3,5-dimethylpyrazol-1-yl | H | H | H | H | 4-NO₂-C₆H₄ | <250° C. |

| | | | | | | | | | |
|---|---|---|---|---|---|---|---|---|---|
| 119 | 4-Cl | · | H | O | 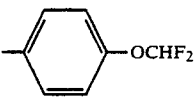 | H H H H | 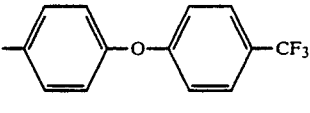 | 224° C. |
| 120 | 4-F | | H | O | 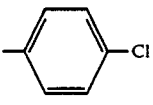 | H H H H | 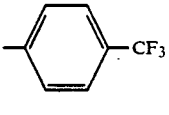 | <250° C. |
| 121 | 4-F | | H | O | 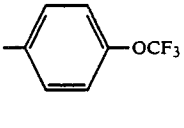 | H H H H | 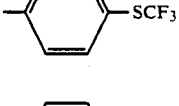 | 201–202° C. |
| 122 | 4-F | | H | O | | H H H H | | 201–202° C. |
| 123 | 4-F | | H | O | | H H H H | | 207–208° C. |
| 124 | 4-F | | H | O | | H H H H | | 220–222° C. |
| 125 | 4-F | | H | O | | H H H H | | 193–194° C. |
| 126 | 4-F | | H | O | | H H H H | 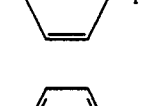 | 214–215° C. |
| 127 | 4-F | | H | O | | H H H H |  | 201° C. |
| 128 | 4-F | | H | O | | H H H H | 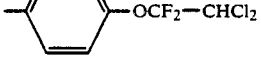 | 199° C. |
| 129 | 4-OCF$_2$—CHFCl | | H | O | 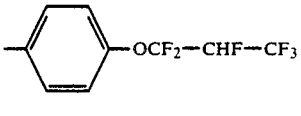 | H H H H | 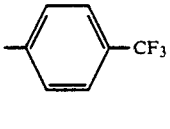 | |
| 130 | 4-OCF$_2$—CHFCl | | H | O | | H H H H | 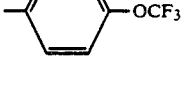 | |

| | | | | | | | | | |
|---|---|---|---|---|---|---|---|---|---|
| 131 | 4-OCF$_2$—CHF—CF$_3$ | H | O | ![pyrazole] -N-N= / \\ =/ | H | H | H | H | ![phenyl-CF$_3$] 4-CF$_3$-C$_6$H$_4$ | |
| 132 | H | H | O | ![pyrazole] | H | H | H | H | ![phenyl-CF$_3$] 4-CF$_3$-C$_6$H$_4$ | |
| 133 | 4-Br | H | O | ![pyrazole] | H | H | H | H | ![phenyl-OCF$_3$] 4-OCF$_3$-C$_6$H$_4$ | |
| 134 | 4-F | H | O | ![pyrazole] | H | H | H | H | ![3-F-4-CF$_3$-phenyl] | 218° C. |
| 135 | 4-F | H | O | ![pyrazole] | H | H | H | H | ![phenyl-SCF$_2$Cl] 4-SCF$_2$Cl-C$_6$H$_4$ | 234° C. |
| 136 | 4-F | H | O | ![4-Cl-pyrazole] | H | H | H | H | ![phenyl-OCF$_2$CHFCl] 4-OCF$_2$—CHFCl-C$_6$H$_4$ | 212° C. |
| 137 | 4-F | H | O | ![4-Cl-pyrazole] | H | H | H | H | ![phenyl-OCF$_2$CHCl$_2$] 4-OCF$_2$—CHCl$_2$-C$_6$H$_4$ | 200° C. |
| 138 | 4-F | H | O | ![4-Cl-pyrazole] | H | H | H | H | ![phenyl-SCF$_2$Cl] 4-SCF$_2$Cl-C$_6$H$_4$ | 212° C. |
| 139 | 4-F | H | O | ![4-Cl-pyrazole] | H | H | H | H | ![phenyl-OCF$_2$CHFCF$_3$] 4-OCF$_2$—CHF—CF$_3$-C$_6$H$_4$ | 206° C. |
| 140 | 4-F | H | O | ![4-Cl-pyrazole] | H | H | H | H | ![3-F-4-CF$_3$-phenyl] | 202° C. |
| 141 | 4-OCH$_2$CF$_3$ | H | O | ![4-Cl-pyrazole] | H | H | H | H | ![phenyl-CF$_3$] 4-CF$_3$-C$_6$H$_4$ | |

| No. | col2 | col3 | col4 | heterocycle | col6 | col7 | col8 | col9 | Ar | mp |
|---|---|---|---|---|---|---|---|---|---|---|
| 142 | 4-OCF$_2$—CHFCl | H | O | N-pyrazole-Cl | H | H | H | H | 4-CF$_3$-C$_6$H$_4$ | |
| 143 | 4-OCF$_2$—CHF—CF$_3$ | H | O | N-pyrazole-Cl | H | H | H | H | 4-OCF$_3$-C$_6$H$_4$ | |
| 144 | 4-OCF$_2$Cl | H | O | N-pyrazole-Cl | H | H | H | H | 4-CF$_3$-C$_6$H$_4$ | |
| 145 | 4-F | H | O | N-triazole | H | H | H | H | 3-F-4-CF$_3$-C$_6$H$_3$ | 217° C. |
| 146 | 4-F | H | O | N-triazole | H | H | H | H | 4-SCF$_2$Cl-C$_6$H$_4$ | 202° C. |
| 147 | 4-Cl | H | O | N-triazole | H | H | H | H | 4-OCF$_2$—CHFCl-C$_6$H$_4$ | 202° C. |
| 148 | 4-Cl | H | O | N-triazole | H | H | H | H | 4-OCF$_2$—CHCl$_2$-C$_6$H$_4$ | 199° C. |
| 149 | 4-Cl | H | O | N-triazole | H | H | H | H | 4-OCF$_2$—CHF—CF$_3$-C$_6$H$_4$ | 203° C. |
| 150 | 4-Cl | H | O | N-triazole | H | H | H | H | 3-F-4-CF$_3$-C$_6$H$_3$ | 224° C. |
| 151 | 4-OCF$_2$—CHFCl | H | O | N-triazole | H | H | H | H | 4-OCF$_3$-C$_6$H$_4$ | |
| 152 | 4-Cl | H | O | N-triazole | H | H | H | H | 4-SCF$_2$Cl-C$_6$H$_4$ | 214° C. |
| 153 | 4-OCHF$_2$ | H | O | N-triazole | H | H | H | H | 4-OCF$_2$—CHFCl-C$_6$H$_4$ | 206° C. |

| | | | | | | | | | |
|---|---|---|---|---|---|---|---|---|---|
| 154 | 4-OCHF$_2$ | H | O | -N(N=CH-N=CH) (1,2,4-triazol-1-yl) | H | H | H | H | 4-SCF$_2$Cl-C$_6$H$_4$ | 226° C. |
| 155 | 4-OCHF$_2$ | H | O | -N(N=CH-N=CH) (1,2,4-triazol-1-yl) | H | H | H | H | 4-(OCF$_2$-CHF-CF$_3$)-C$_6$H$_4$ | 205° C. |
| 156 | 4-Br | H | O | -N(N=CH-N=CH) (1,2,4-triazol-1-yl) | H | H | H | H | 4-Cl-C$_6$H$_4$ | 224° C. |
| 157 | 4-Br | H | O | -N(N=CH-N=CH) (1,2,4-triazol-1-yl) | H | H | H | H | 4-CF$_3$-cyclohexyl | Harz |
| 158 | 4-Br | H | O | -N(N=CH-CH=CH) (pyrazol-1-yl) | H | H | H | H | 4-SCF$_3$-C$_6$H$_4$ | 211° C. |
| 159 | 4-Br | H | O | -N(N=CH-CH=CH) (pyrazol-1-yl) | H | H | H | H | 4-Cl-C$_6$H$_4$ | 187° C. |
| 160 | 4-Br | H | O | -N(N=CH-N=CH) (1,2,4-triazol-1-yl) | H | H | H | H | 4-OCHF$_2$-C$_6$H$_4$ | 225° C. |
| 161 | 4-Br | H | O | -N(N=CH-CCl=CH) (4-chloropyrazol-1-yl) | H | H | H | H | 4-SCF$_2$Cl-2-Cl-C$_6$H$_3$ | 215° C. |
| 162 | 4-Br | H | O | -N(N=CH-CH=CH) (pyrazol-1-yl) | H | H | H | H | 4-F-C$_6$H$_4$ | 216° C. |
| 163 | 4-Br | H | O | -N(N=CH-CH=CH) (pyrazol-1-yl) | H | H | H | H | 4-OCHF$_2$-C$_6$H$_4$ | 216° C. |
| 164 | 4-Br | H | O | -N(N=CH-CH=CH) (pyrazol-1-yl) | H | H | H | H | 4-SCF$_2$Cl-2-Cl-C$_6$H$_3$ | — |
| 165 | 4-Br | H | S | -N(N=CH-CH=CH) (pyrazol-1-yl) | H | H | H | H | 4-CF$_3$-cyclohexyl | 161° C. |

| # | R1 | | | Het | | | | | R2 | mp |
|---|---|---|---|---|---|---|---|---|---|---|
| 166 | 4-Cl | H | O | pyrazole-Cl | H | H | H | H | —CH₂—CH₂—O—CH₂—CF₃ | |
| 167 | —OCHF₂ | H | O | pyrazole-Cl | H | H | H | H | —CH₂—CH₂—O—CH₂—CF₃ | |
| 168 | 4-Cl | H | O | pyrazole-CH₃ | H | H | H | H | 4-Cl-C₆H₄ | |
| 169 | —OCHF₂ | H | O | pyrazole-Cl,Cl | H | H | H | H | 4-F-C₆H₄ | |
| 170 | 4-OCF₂—CHFCl | H | O | pyrazole-Cl | H | H | H | H | 4-Cl-C₆H₄ | 200° C. |
| 171 | 4-OCF₂—CHFCl | H | O | pyrazole-Cl | H | H | H | H | 4-CF₃-C₆H₄ | 210° C. |
| 172 | 4-OCF₂—CHFCl | H | O | triazole | H | H | H | H | 4-CF₃-C₆H₄ | 248° C. |
| 173 | 4-OCF₂—CHFCl | H | O | triazole | H | H | H | H | 4-OCF₃-C₆H₄ | |
| 174 | 4-Br | H | O | pyrazole-Cl | H | H | H | H | 4-OCF₂Cl-C₆H₄ | 223° C. |
| 175 | 4-OCHF₂ | H | O | pyrazole-Br | H | H | H | H | 4-CF₃-C₆H₄ | 152° C. |
| 176 | 4-OCHF₂ | H | O | pyrazole-Br | H | H | H | H | 4-OCF₃-C₆H₄ | 211° C. |

-continued
| | | | | | | | | | |
|---|---|---|---|---|---|---|---|---|---|
| 177 | 4-OCHF$_2$ | H | O | 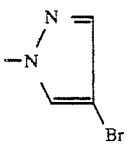 | H | H | H | H | 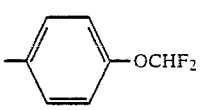 | 169° C. |
| 178 | 4-OCHF$_2$ | H | O | 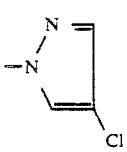 | H | H | H | H | 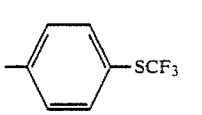 | 226° C. |
| 179 | 4-Br | H | O | 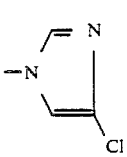 | H | H | H | H | 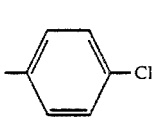 | |
| 180 | 4-Br | H | O | 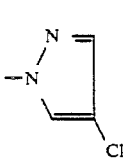 | H | H | H | H | 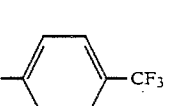 | 202° C. |
| 181 | 4-Br | H | O | 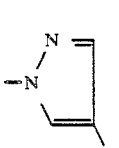 | H | H | H | H | 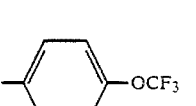 | 249° C. |
| 182 | 4-OCHF$_2$ | H | O | 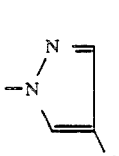 | H | H | H | H | 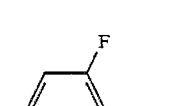 | 201° C. |
| 183 | H | H | O | 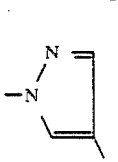 | H | H | H | H | 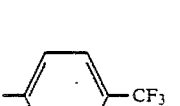 | 227° C. |
| 184 | 4-Cl | H | O | 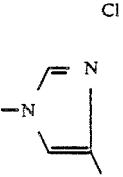 | H | H | H | H | 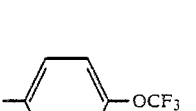 | 243° C. |
| 185 | H | H | O | 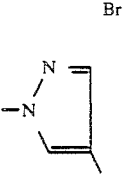 | H | H | H | H | 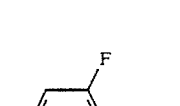 | 219° C. |
| 186 | 4-Br | H | O | 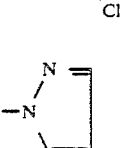 | H | H | H | H |  | |

-continued
| | | | | | | | | |
|---|---|---|---|---|---|---|---|---|
| 187 | 4-Br | H | O | 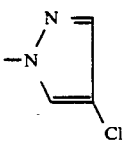 | H H H H | 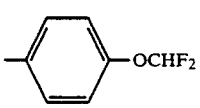 | | 208° C. |
| 188 | 4-Br | H | O | 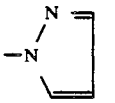 | H H H H | 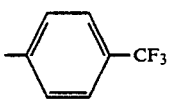 | | 224° C. |
| 189 | 4-Br | H | O | 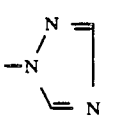 | H H H H | 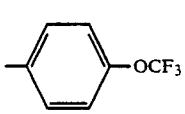 | | |
| 190 | 4-Br | H | O | 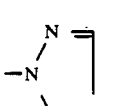 | H H H H | 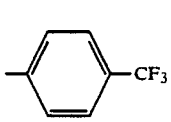 | | 249° C. |
| 191 | 4-OCHF$_2$ | H | O | 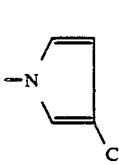 | H H H H | 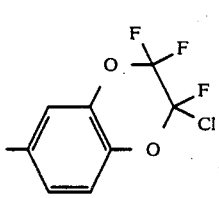 | | |
| 192 | 4-OCHF$_2$ | H | O | 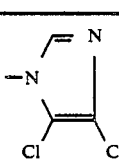 | H H H H | 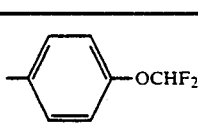 | | |
| 193 | 4-OCHF$_2$ | H | O | 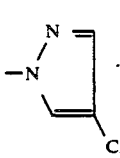 | H H H H | 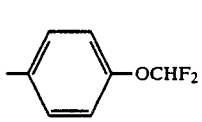 | | 180° C. |
| 194 | 4-OCHF$_2$ | H | O | 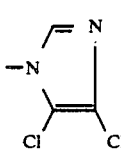 | H H H H | 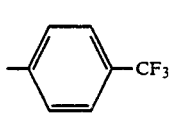 | | |
| 195 | 4-OCHF$_2$ | H | O | 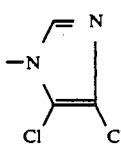 | H H H H | 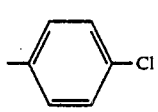 | | |
| 196 | 4-OCHF$_2$ | H | O | 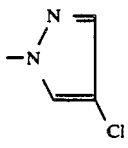 | H H H H | 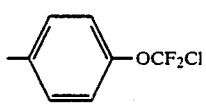 | | 201° C. |

-continued

| | | | | | | | | | |
|---|---|---|---|---|---|---|---|---|---|
| 197 | 4-Cl | H | O | -N=N-CH=C(Br)- (pyrazole ring) | H | H | H | H | 4-CF₃-C₆H₄ | 242° C. |
| 198 | 4-Cl | H | O | -N-N=CH-C(Br)= (pyrazole) | H | H | H | H | 4-Cl-C₆H₄ | 212° C. |
| 199 | 4-OCHF₂ | H | O | pyrazole-Br | H | H | H | H | 4-Cl-C₆H₄ | 219° C. |
| 200 | 4-Br | H | O | pyrazole | H | H | H | H | 4-OCF₃-C₆H₄ | 219° C. |
| 201 | 4-Br | H | O | pyrazole-Cl | H | H | H | H | 1,2-(OCF₂CF₂Cl)-benzo | 217° C. |
| 202 | 4-OCHF₂ | H | O | -N=N-C(Cl)=C(Cl)- | H | H | H | H | 4-OCF₃-C₆H₄ | — |
| 203 | 4-Br | H | O | pyrazole | H | H | H | H | 4-CF₃-cyclohexyl | Öl |
| 204 | H | H | O | pyrazole-Cl | H | H | H | H | 4-OCF₃-C₆H₄ | 218° C. |
| 205 | H | H | O | pyrazole-Br | H | H | H | H | 4-OCF₃-C₆H₄ | 223° C. |
| 206 | H | H | O | pyrazole-Br | H | H | H | H | 4-CF₃-C₆H₄ | 245° C. |
| 206a | 4-F | H | O | pyrazole-Cl | H | H | H | H | 4-SCF₃-C₆H₄ | — |

| 207 | 4-OCH₃ | H | O | 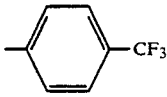 | H H H H | 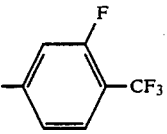 | 221° C. |
| --- | --- | --- | --- | --- | --- | --- | --- |
| 208 | 4-OCH₃ | H | O | 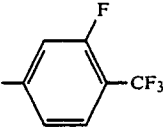 | H H H H | 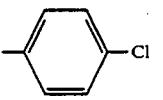 | 238° C. |
| 209 | 4-OCHF₂ | H | O | 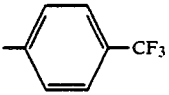 | H H H H | 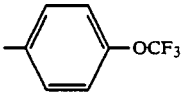 | 252° C. |
| 210 | 4-OCH₃ | H | O | 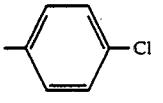 | H H H H | 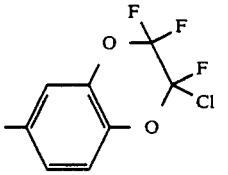 | 221° C. |
| 211 | 4-OCH₃ | H | O | | H H H H | | 250° C. |
| 212 | 4-OCH₃ | H | O | | H H H H | | 210° C. |
| 213 | 4-OCH₃ | H | O | | H H H H | | 201° C. |
| 214 | 4-OCH₃ | H | O | | H H H H | 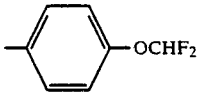 | 186° C. |
| 215 | H | H | O | | H H H H | | 212° C. |
| 216 | H | H | O | | H H H H | | 233° C. |
| 217 | H | H | O | 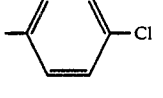 | H H H H | 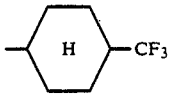 | 236° C. |

| | | | | | | | | | |
|---|---|---|---|---|---|---|---|---|---|
| 218 | H | H | O | 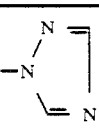 | H | H | H | H | 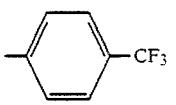 | 215° C. |
| 219 | H | H | O | 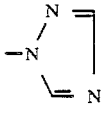 | H | H | H | H | 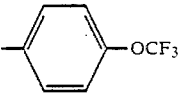 | 245° C. |
| 220 | 4-OC$_2$H$_5$ | H | O | 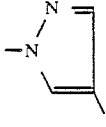 | H | H | H | H | 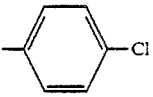 | 179° C. |
| 221 | 4-OC$_2$H$_5$ | H | O | 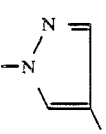 | H | H | H | H | 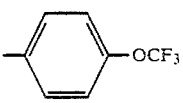 | 153° C. |
| 222 | 4-OC$_2$H$_5$ | H | O | 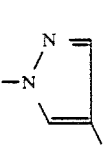 | H | H | H | H | 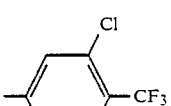 | 176° C. |
| 223 | 3-CH$_3$ | H | O | 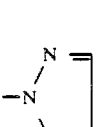 | H | H | H | H | 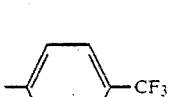 | 224° C. |
| 224 | 3-CH$_3$ | H | O |  | H | H | H | H |  | 190° C. |
| 225 | 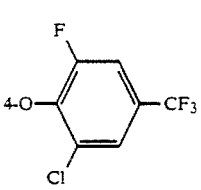 | H | O | 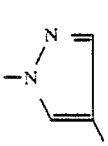 | H | H | H | H | 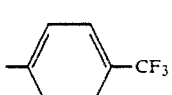 | 208° C. |
| 226 | 4-Cl | H | O | 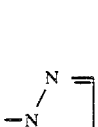 | H | H | H | H | 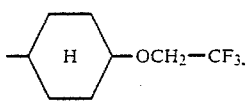 | 164° C. |
| 227 | 4-OCHF$_2$ | H | O | 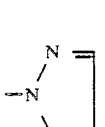 | H | H | H | H | 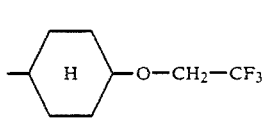 | Öl |
| 228 | 4-Cl | H | O | 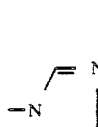 | H | H | H | H | 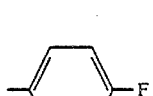 | 197° C. |

| | | | | | | | | | |
|---|---|---|---|---|---|---|---|---|---|
| 229 | 4-Cl | H | O | —N=CH-C(CF₃)=CH-N (pyrazole with CF₃) | H | H | H | H | 4-Cl-C₆H₄ | 215° C. |
| 230 | 4-Cl | H | O | —N=CH-C(CF₃)=CH-N | H | H | H | H | 4-CF₃-C₆H₄ | 248° C. |
| 231 | 4-Cl | H | O | —N=CH-C(CF₃)=CH-N | H | H | H | H | 4-OCF₃-C₆H₄ | 188° C. |
| 232 | 4-Cl | H | O | —N=CH-C(CF₃)=CH-N | H | H | H | H | 4-SCF₃-C₆H₄ | 227° C. |
| 233 | 4-Cl | H | O | —N=CH-C(J)=CH-N | H | H | H | H | 4-Cl-C₆H₄ | 234° C. |
| 234 | 4-Cl | H | O | —N-N=CH-C(J)=CH | H | H | H | H | 4-OCF₃-C₆H₄ | 232° C. |
| 235 | 4-Cl | H | O | —N-N=CH-C(J)=CH | H | H | H | H | 4-SCF₃-C₆H₄ | 218° C. |
| 236 | 4-Cl | H | O | —N-N=CH-C(J)=CH | H | H | H | H | 4-CF₃-C₆H₄ | 188° C. |
| 237 | 4-Cl | H | O | —N-N=CH-C(J)=CH | H | H | H | H | 4-CF₃-cyclohexyl | 184° C. |
| 238 | H | H | O | —N-N=CH-C(Cl)=CH | H | H | H | H | 3,4-(CF₃)₂-C₆H₃ | 234° C. |

-continued

| | | | | | | | | | |
|---|---|---|---|---|---|---|---|---|---|
| 239 | 4-Cl | H | O | N-pyrazole-Cl | H | H | H | H | 4-Br-phenyl | 217° C. |
| 240 | 4-OCHF$_2$ | H | O | N-pyrazole | H | H | H | H | 4-Br-phenyl | 224° C. |
| 241 | 4-F | H | O | N-pyrazole-Cl | H | H | H | H | 4-Br-phenyl | 195° C. |
| 242 | 4-Cl | H | O | N-triazole | H | H | H | H | 4-Br-phenyl | 205° C. |
| 243 | 4-OCHF$_2$ | H | O | N-pyrazole-Cl | H | H | H | H | 4-Br-phenyl | 188° C. |
| 244 | H | H | O | N-pyrazole-Cl | H | H | H | H | 4-NO$_2$-phenyl | >250° C. |
| 245 | H | H | O | N-pyrazole-Cl | H | H | H | H | 2-Cl-4-OCF$_3$-phenyl | 180° C. |
| 245a | H | H | O | N-pyrazole-Cl | H | H | H | H | 2-Cl-4-SCF$_2$Cl-phenyl | — |
| 246 | H | H | O | N-pyrazole-Cl | H | H | H | H | 4-Br-phenyl | 201° C. |
| 247 | 3,4-OCH$_2$O | | O | N-pyrazole-Cl | H | H | H | H | 4-Cl-phenyl | >250° C. |
| 248 | 3,4-OCH$_2$O | | O | N-pyrazole-Cl | H | H | H | H | 4-CF$_3$-phenyl | 226° C. |

-continued

| | | | | | | | | | | |
|---|---|---|---|---|---|---|---|---|---|---|
| 249 | 4-Br | | H | O | -N-N=CH-C(Br)=CH (pyrazole, 4-Br) | H | H | H | H | 4-Cl-phenyl | 215° C. |
| 250 | 4-Br | | H | O | -N-N=CH-C(Br)=CH (pyrazole, 4-Br) | H | H | H | H | 4-Br-phenyl | 225° C. |
| 250a | H | | H | O | -N-N=CH-C(Br)=CH (pyrazole, 4-Br) | H | H | H | H | 3-Cl-4-OCF$_3$-phenyl | |
| 251 | 4-Br | | H | O | -N-N=CH-C(Br)=CH (pyrazole, 4-Br) | H | H | H | H | 4-CF$_3$-phenyl | 222° C. |
| 252 | 4-Br | | H | O | -N-N=CH-C(Br)=CH (pyrazole, 4-Br) | H | H | H | H | 4-OCF$_3$-phenyl | 235° C. |
| 252 | 4-Br | | H | O | -N-N=CH-C(Br)=CH (pyrazole, 4-Br) | H | H | H | H | 4-OCF$_3$-phenyl | 235° C. |
| 253 | 3,4-OCF$_2$O | | | O | -N-N=CH-C(Cl)=CH (pyrazole, 4-Cl) | H | H | H | H | 4-Cl-phenyl | >250° C. |
| 254 | 3,4-OCF$_2$O | | | O | -N-N=CH-C(Cl)=CH (pyrazole, 4-Cl) | H | H | H | H | 4-CF$_3$-phenyl | 199° C. |
| 255 | 3,4-OCF$_2$O | | | O | -N-N=CH-C(Br)=CH (pyrazole, 4-Br) | H | H | H | H | 4-OCF$_3$-phenyl | 178° C. |
| 256 | 4-OCHF$_2$ | | H | O | -N-N=CH-C(Cl)=CH (pyrazole, 4-Cl) | H | H | H | H | phenyl | |

-continued

| # | R1 | | | | | | Ar | m.p. |
|---|---|---|---|---|---|---|---|---|
| 257 | H | H | O | pyrazole-Cl | H | H H H | 3,4-bis(OCF₃)-phenyl | 170° C. |
| 258 | H | H | O | pyrazole-Cl | H | H H H | 2-F, 5-CN-phenyl | 235° C. |
| 259 | H | H | O | pyrazole-Cl | H | H H H | 3,4-diF-phenyl | 208° C. |
| 259a | 3,4-OCF₂O | H | O | pyrazole-Br | H | H H H | 4-CF₃-phenyl | 208° C. |
| 260 | 4-F | H | O | pyrazole-Br | H | H H H | 4-OCF₃-phenyl | 222° C. |
| 261 | H | H | O | pyrazole-Cl | H | H H H | 4-C(CH₃)₃-phenyl | 198° C. |
| 262 | 4-OCHF₂ | H | O | pyrazole-Cl | H | H H H | 4-C(CH₃)₃-phenyl | 235° C. |
| 263 | 4-Cl | H | O | pyrazole-Cl | H | H H H | 4-C(CH₃)₃-phenyl | 192° C. |
| 264 | 3,4-OCH₃ | H | O | pyrazole-Cl | H | H H H | 4-CF₃-phenyl | 216° C. |
| 265 | 3-Cl | H | O | pyrazole-Cl | H | H H H | 4-Cl-phenyl | 192° C. |

-continued

| | | | | | | | | | |
|---|---|---|---|---|---|---|---|---|---|
| 266 | 3-Cl | H | O | 3-chloro-pyrazol-1-yl | H | H | H | H | 4-CF₃-phenyl | 195° C. |
| 267 | 4-OCF₃ | H | O | 3-chloro-pyrazol-1-yl | H | H | H | H | 4-Cl-phenyl | 178° C. |
| 268 | 4-OCF₃ | H | O | 3-chloro-pyrazol-1-yl | H | H | H | H | 4-CF₃-phenyl | 174° C. |
| 269 | 4-OCF₃ | H | O | 3-chloro-pyrazol-1-yl | H | H | H | H | 4-OCF₃-phenyl | 170° C. |
| 270 | 4-CF₃ | H | O | 3-chloro-pyrazol-1-yl | H | H | H | H | 4-Cl-phenyl | 233° C. |
| 271 | 4-CF₃ | H | O | 3-chloro-pyrazol-1-yl | H | H | H | H | 4-CF₃-phenyl | 107° C. |
| 272 | 4-CF₃ | H | O | 3-chloro-pyrazol-1-yl | H | H | H | H | 4-OCF₃-phenyl | 224° C. |
| 273 | 4-Cl | H | O | 3-chloro-1,2,4-triazol-1-yl | H | H | H | H | 4-Cl-phenyl | >250° C. |
| 274 | 4-Cl | H | O | 3-chloro-1,2,4-triazol-1-yl | H | H | H | H | 4-CF₃-phenyl | 203° C. |
| 274a | 4-Cl | H | O | 3-chloro-1,2,4-triazol-1-yl | H | H | H | H | 4-OCF₃-phenyl | |

-continued

| | | | | | | | | | |
|---|---|---|---|---|---|---|---|---|---|
| 275 | 4-Cl | H | O | pyrazole-Cl (N=N-N, =N) | H | H | H | H | 4-OCHF₂-phenyl | 221° C. |
| 276 | 4-OCHF₂ | H | O | pyrazole-J (N-N) | H | H | H | H | 4-Br-phenyl | 184° C. |
| 277 | 4-OCHF₂ | H | O | pyrazole-J (N-N) | H | H | H | H | 4-CF₃-phenyl | |
| 277a | 4-OCHF₂ | H | O | pyrazole (N-N) | H | H | H | H | 4-OCF₃-phenyl | |
| 277b | 4-F | H | O | pyrazole-Cl (N-N) | H | H | H | H | 4-OCHF₂-phenyl | |
| 277c | 4-Cl | H | O | pyrazole (N-N, =N) | H | H | H | H | 4-SCF₂Cl-phenyl | |
| 277d | 4-F | H | O | pyrazole (N-N) | H | H | H | H | 4-OCF₂—CHFCl-phenyl | |
| 277e | 3,4-O-CF₂-O | H | O | pyrazole-Cl (N-N) | H | H | H | H | 4-OCF₃-phenyl | |

EXAMPLE 278

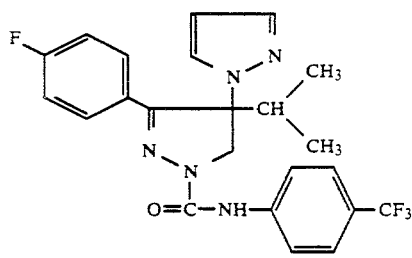

5 g (0.012 mol) of the 4-trifluoromethylanilide of 3-(4-fluorophenyl)-4-(1H-pyrazol-1-yl)-4,5-dihydro-1-pyrazolecarboxylic acid are dissolved in 80 ml of (anhydrous) tetrahydrofuran, and 16.5 ml (0.026 mol) of a 15-percent butyllithium solution in hexane are added with stirring at −15° C. under an argon atmosphere. Stirring is continued for one hour at −15° C., and 5 ml (0.05) mol of 2-iodopropane are then added at −15° C. The reaction mixture is then heated to room temperature (about 20° C.), and, after 30 minutes, 50 ml of water are added. The mixture is subsequently extracted with 100 ml of ether, the ether phase is dried, and the solvent is distilled off in vacuo. The oily residue is chromatographed over silica gel using hexane/acetone (7:3). 3.3 g of the 4-trifluoromethylanilide of 3-(4-fluorophenyl)-4-(1H-pyrazol-1-yl)-4-isopropyl-4,5-dihydro-1-pyrazolecarboxylic acid are obtained as a colourless foam. M.p. 125° C.

¹H-NMR (CDCl₃, TMS, ppm) 8.236 (1H,s), 7.66–7.0 (10H, m), 6.388 (1H,t), 4.535–4.378 (2H, q), 3.3–3.2(1H,m), 1.23 (3H, d) and 1.91 (3H, d).

The following can be prepared in an analogous manner:

General Formula (I)

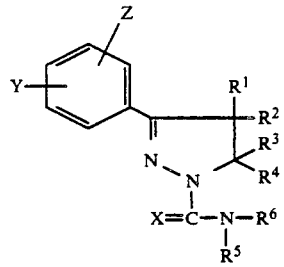

| Ex. No. | Y | Z | X | R¹ | R² | R³ | R⁴ | R⁵ | R⁶ | M.p. |
|---|---|---|---|---|---|---|---|---|---|---|
| 279 | 4-F | H | O | 1H-Pyrazol-1-yl | CH$_3$ | H | H | H | 4-CF$_3$-C$_6$H$_4$ | 182–184° C. |
| 280 | 4-Cl | H | O | 1H-Pyrazol-1-yl | CH$_3$ | H | H | H | 4-CF$_3$-C$_6$H$_4$ | |
| 281 | 4-OCHF$_2$ | H | O | 1H-Pyrazol-1-yl | CH$_3$ | H | H | H | 4-OCF$_3$-C$_6$H$_4$ | |
| 282 | 4-F | H | O | 1H-Pyrazol-1-yl | COOCH$_3$ | H | H | H | 4-CF$_3$-C$_6$H$_4$ | |
| 283 | 4-OCHF$_2$ | H | O | 1H-Pyrazol-1-yl | COOCH$_3$ | H | H | H | 4-Cl-C$_6$H$_4$ | |
| 284 | 4-F | H | O | 1,2,4-1H-Triazol-1-yl | CH$_3$ | H | H | H | 4-OCF$_3$-C$_6$H$_4$ | |
| 285 | 4-F | H | O | 1,2,4-1H-Triazol-1-yl | —CH(CH$_3$)$_2$ | H | H | H | 4-OCF$_3$-C$_6$H$_4$ | 135° C. |
| 286 | 4-Cl | H | O | 4-Chlor-1H-Pyrazol-1-yl | —CH$_3$ | H | H | H | 4-OCHF$_2$-C$_6$H$_4$ | 180–182° C. |
| 287 | 4-F | H | O | 4-Chlor-1H-pyrazol-1-yl | —COOCH$_3$ | H | H | H | 4-OCF$_3$-C$_6$H$_4$ | 169° C. |
| 288 | 4-F | H | O | 4-Chlor-1H-pyrazol-1-yl | —Si(CH$_3$)$_3$ | H | H | H | 4-OCF$_3$-C$_6$H$_4$ | resin |

-continued

General Formula (I)

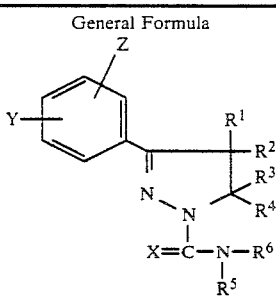

| Ex. No. | Y | Z | X | R¹ | R² | R³ | R⁴ | R⁵ | R⁶ | M.p. |
|---|---|---|---|---|---|---|---|---|---|---|
| 288a | 4-OCHF₂ | H | O | 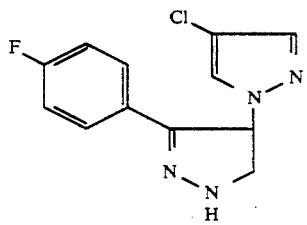 | —Si(CH₃)₃ | H | H | H | 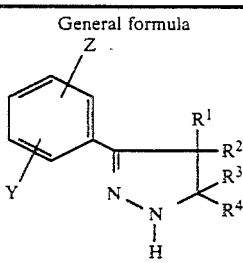 | resin |

Preparation of Starting Compounds

EXAMPLE 1A 6 g (0.024 mol) of 4'-fluoro-2-(1"H-4"-chloropyrazol-1"-yl)-acrylophenone are dissolved in 60 ml of ethanol, and 3 ml of hydrazine hydrate are added with stirring. During this process, the temperature is maintained at 40°–45° C. while cooling with a water-bath. Stirring is continued for 30 minutes, and the ethanol is subsequently distilled off in vacuo. 150 ml of methylene chloride are added to the residue, the mixture is shaken, and the methylene chloride phase is then separated off and dried over magnesium sulphate. The solvent is subsequently distilled off in vacuo, and the oily residue is crystallized with toluene/ethyl acetate (10:1). 3.5 g of 3-(4'-fluorophenyl)-4-(1"H-4"-chloropyrazol-1"-yl)-4,5-dihydropyrazole are obtained as pale yellow crystals of melting point 127°–128° C.

The following pyrazolines are obtained in an analogous manner:

General formula

| Ex. No. | Y | Z | R¹ | R² | R³ | R⁴ | Physical constants |
|---|---|---|---|---|---|---|---|
| 2A | 4-OCHF₂ | H | 1-H-pyrazol-1-yl | H | H | H | oil |
| 3A | 4-OCHF₂ | H | 1,2,4-1H-triazol-1-yl | H | H | H | oil |
| 4A | 4-Cl | H | 1H-pyrazol-1-yl | H | H | H | oil, ¹H-NMR (CDCl₃): 7.15–7.55(6H, m) 6.22(1H, s), 6.0(1H, q), 3.73–3.94 (2H, m) |
| 5A | 4-OCHF₂ | H | 1H-4-chloro-pyrazol-1-yl | H | H | H | oil, ¹H-NMR (CDCl₃): 7.61 (2H, d) 7.08(2H, d), 7.33(1H, s), 7.44(1H, s), 6.51(1H, t) 5.92(1H, q), 3.72–3.9(2H, m) |
| 6A | 4-Cl | H | 1H-4-chloro-pyrazol-1-yl | H | H | H | M.p.: 177° C. |
| 7A | 4-F | H | 1,2,4-1H-triazol-1-yl | H | H | H | M.p.: 116–118° C. |
| 8A | 4-Cl | H | 1,2,4-1H-triazol-1-yl | H | H | H | M.p.: 175° C. |
| 9A | 4-F | H | 1-H-pyrazol-1-yl | H | H | H | M.p.: 130° C. |
| 10A | 4-OCF₃ | H | 1,2,4-1H-triazol-1-yl | H | H | H | oil |
| 11A | 4-Cl | H | 3,5-dimethyl-1H-pyrazol-1-yl | H | H | H | oil, ¹H-NMR(CDCl₃, TMS): 17.20–7.40(4H, m) 6,04–5.98(1H, 1); 4.19(1H, s); 4.03–3.69(2H, m) 2.20(3H, s); 2.18(3H, s) |

-continued

General formula

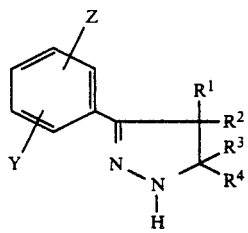

| Ex. No. | Y | Z | R¹ | R² | R³ | R⁴ | Physical constants |
|---|---|---|---|---|---|---|---|
| 12A | 4-F | H | 3,5-dimethyl-1H-pyrazol-1-yl | H | H | H | oil |
| 13A | H | H | 1H-pyrazol-1-yl | H | H | H | |
| 14A | H | H | 1,2,4-1H-triazol-1-yl | H | H | H | |
| 15A | 4-Br | H | 1H-pyrazol-1-yl | H | H | H | |
| 16A | 4-CF₃ | H | 1H-pyrazol-1-yl | H | H | H | |
| 17A | 4-CF₃ | H | 4-chloro-1H-pyrazol-1-yl | H | H | H | |
| 18A | 4-CF₃ | H | 1,2,4-1H-triazol-1-yl | H | H | H | |
| 19A | 4-CF₃ | H | 1H-pyrazol-1-yl | H | H | H | |
| 20A | 4-Br | H | 1,2,4-1H-Triazol-1-yl | H | H | H | M.p. 163° C. |
| 21A | 4-Br | H | 1H-4-Chlor-pyrazol-1-yl | H | H | H | M.p. 189° C. |
| 22A | 4-F | H | 1,2,3,4-2H-Tetrazol-2-yl | H | H | H | |
| 23A | 4-OCH₂CF₃ | H | 1H-Pyrazol-1-yl | H | H | H | |
| 24A | 4-Cl | H | 1,2,4-4H-Triazol-1-yl | H | H | H | |
| 25A | 4-Cl | H | 1,2,4-1H-Triazol-1-yl | H | CH₃ | H | |
| 26A | 4-F | H | 1H-Pyrazol-1-yl | H | CH₃ | CH₃ | |
| 27A | 4-OCF₂—CHFCl | H | 1H-4-Chlor-pyrazol-1-yl | H | H | H | |
| 28A | 4-Cl | H | ![pyrazole with CH₃] | H | H | H | Oil |
| 29A | 4-OCHF₂ | F | ![pyrazole with 2 Cl] | H | H | H | Oil |
| 30A | 4-Br | H | ![pyrazole with Cl] | H | H | H | |
| 31A | 4-OCHF₂ | H | ![pyrazole with Br] | H | H | H | M.p. 219° C. |
| 32A | H | H | ![pyrazole with Cl] | H | H | H | M.p. 139° C. |
| 33A | 4-Cl | H | ![pyrazole with Br] | H | H | H | |

-continued
General formula
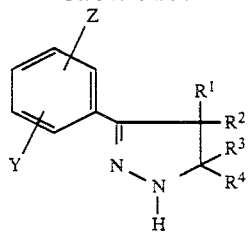
| Ex. No. | Y | Z | R¹ | R² | R³ | R⁴ | Physical constants |
|---|---|---|---|---|---|---|---|
| 34A | H | H | —N(N=)—CH=C(Br)— | H | H | H | |
| 35A | 4-OCH$_3$ | H | —N(N=)—CH=N— | H | H | H | Oil |
| 36A | 4-OCH$_3$ | H | —N(N=)—CH=C(Br)— | H | H | H | Oil |
| 37A | 4-OCH$_3$ | H | —N(N=)—CH=C(Cl)— | H | H | H | Oil |
| 38A | 4-OCH$_3$ | H | —N(N=)—CH=CH— | H | H | H | Oil |
| 39A | 4-OC$_2$H$_5$ | H | —N(N=)—CH=C(Br)— | H | H | H | |
| 40A | 3-CH$_3$ | H | —N(N=)—CH=C(Cl)— | H | H | H | Oil |
| 41A | 2-F, 6-Cl, 4-CF$_3$ (4-O-phenyl) | H | —N(N=)—CH=C(Cl)— | H | H | H | Oil |
| 42A | 4-Cl | H | —N(N=)—CH=C(CF$_3$)— | H | H | H | |

-continued
General formula
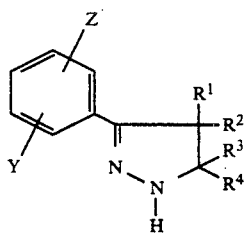
| Ex. No. | Y | Z | R¹ | R² | R³ | R⁴ | Physical constants |
|---------|---|---|----|----|----|----|-------------------|
| 43A | 4-Cl | H | —N(pyrazole)-J | H | H | H | |
| 44A | 4-Br | H | —N(pyrazole)-Br | H | H | H | M.p. 189° C. |
| 45A | 3,4-O-CH₂-O | | —N(pyrazole)-Cl | H | H | H | Oil |
| 46A | 3,4-O-CF₂-O | | —N(pyrazole)-Cl | * | H | H | H | |
| 47A | 3,4-O-CF₂-O | | —N(pyrazole)-Br | H | H | H | Oil |
| 48A | 4-F | H | —N(pyrazole)-Br | H | H | H | Oil |
| 49A | 3,4-OCH₃ | H | —N(pyrazole)-Cl | H | H | H | Oil |
| 50A | 3-Cl | H | —N(pyrazole)-Cl | H | H | H |

-continued

General formula

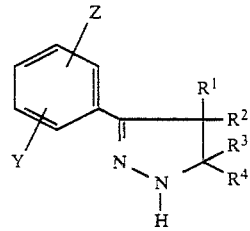

| Ex. No. | Y | Z | R¹ | R² | R³ | R⁴ | Physical constants |
|---|---|---|---|---|---|---|---|
| 51A | 4-OCF₃ | H | ![pyrazole-Cl] | H | H | H | |
| 52A | 4-Cl | H | ![pyrazole-Cl,N] | H | H | H | |
| 53A | 4-OCHF₃ | H | ![pyrazole-J] | H | H | H | |

EXAMPLE 54 A

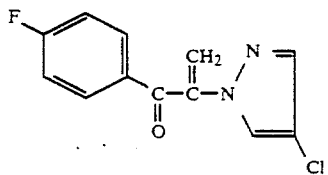

23.9 g (0.1 mol) of α-(1H-4-chloropyrazol-1-yl)-4'-fluoroacetophenone are suspended in 30 ml of methanol at 20° to 30° C. 40 ml of 37 percent strength formalin solution, then 5 ml of piperidine and subsequently 5.5 ml of glacial acetic acid are then added with stirring, during which procedure the temperature rises to 35° to 40° C. The reaction mixture is then stirred at room temperature (about 20° C.) for 4 to 5 hours, until starting material is no longer present according to a thin-layer chromatography check. The reaction mixture is then diluted with ether to 300 ml, and the ether phase is separated off and dried over magnesium sulphate. For purification, the dried ether phase is filtered over silica gel. The ether is subsequently distilled off in vacuo. 16 g of a yellow oil are obtained. The resulting 4'-fluoro-2-(1"H-4"-chloropyrazol-1"-yl) acrylophenone is further reacted without further purification.

¹H-NMR: (CDCl₃, TMS, ppm) 7.85-7.93 (2H,m); 7.09-7.2 (2H,m); 7.60 (1H,s); 7.84 (1H,s); 5.56 (1H,s), 6.34 (1H,s).

The following derivatives can be obtained in an analogous manner:

General formula:

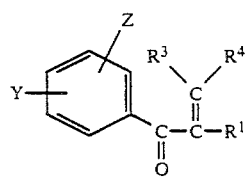

| Ex. No. | Y | Z | R¹ | R² | R³ | R⁴ | Physical constants |
|---|---|---|---|---|---|---|---|
| 55A | 4-OCHF₂ | H | 1,2,4-1H-Triazol-1-yl | | H | H | oil, ¹H-NMR(CDCl₃ 8,68(1H, s); 8.06(1H, s), 7,915(2H, d); 7.25(2H, d) 6,63(1H, t), 6,68(1H, s); 5,8(1H, s) |
| 56A | 4-OCHF₂ | H | 1H-Pyrazol-1-yl | | H | H | oil |
| 57A | 4-Cl | H | 1H-Pyrazol-1-yl | | H | H | oil |
| 58A | 4-Cl | H | 4-Chlor-1H-pyrazol-1-yl | | H | H | oil, (¹H-NMR(CDCl₃) |

-continued

General formula:

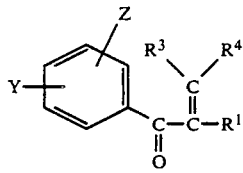

| Ex. No. | Y | Z | R¹ | R² | R³ | R⁴ | Physical constants |
|---|---|---|---|---|---|---|---|
| 59A | 4-OCHF₂ | H | 4-Chlor-1-H-pyrazol-1-yl | | H | H | 6,35(1H, s), 5,58(1H, s) oil |
| 60A | 4-F | H | 1,2,4-1H-Triazol-1-yl | | H | H | oil, ¹H-NMR(CDCl₃) 8,68(1H, s), 8,05(1H, s), 7,89–7,96(2H, m), 7,24–7,17 (2H, m); 6,67(1H, s); 5.79 (1H, s) |
| 61A | 4-Cl | H | 1,2,4-1H-triazol-1-yl | | H | H | M.p.: 122° C. |
| 62A | 4-OCF₃ | H | 1,2,4-1H-triazol-1-yl | | H | H | Oil |
| 63A | 4-Cl | H | 3,5-dimethyl-1H-pyrazol-1-yl | | H | H | Oil |
| 64A | 4-F | H | 3,5-dimethyl-1H-pyrazol-1-yl | | H | H | Oil |
| 65A | 4-F | H | 1H-pyrazol-1-yl | | H | H | Oil |
| 66A | H | H | 1H-pyrazol-1-yl | | H | H | Oil |
| 67A | H | H | 1,2,4-1H-triazol-1-yl | | H | H | Oil |
| 68A | 4-Br | H | 1H-pyrazol-1-yl | | H | H | Oil |
| 69A | 4-CF₃ | H | 1H-pyrazol-1-yl | | H | H | Oil |
| 70A | 4-CF₃ | H | 4-chloro-1H-triazol-1-yl | | H | H | Oil |
| 71A | 4-CF₃ | H | 1,2,4-1H-triazol-1-yl | | H | H | Oil |
| 72A | 4-CH₃ | H | 1H-pyrazol-1-yl | | H | H | Oil |
| 73A | 4-OCH₂CF₃ | H | 1H-pyrazol-1-yl | | H | H | Oil |
| 74A | 4-Br | H | imidazol-1-yl | | H | H | Oil |
| 75A | 4-Br | H | 1H-4-Chlor-pyrazol-1-yl | | H | H | |
| 76A | 4-F | H | 1,2,3,4-2H-Tetrazol-1-yl | | H | H | Oil |
| 77A | 4-Cl | H | 1,2,4-1H-Triazol-1-yl | | CH₃ | H | Oil |
| 78A | 4-F | H | 1H-Pyrazol-1-yl | | CH₃ | CH₃ | Oil |
| 79A | H | H | (N-N pyrazole with Cl) | | H | H | Oil |
| 80A | 4-Cl | H | (N-N pyrazole with Br) | | H | H | Oil |
| 81A | H | H | (N-N pyrazole with Br) | | H | H | Oil |
| 82A | 4-OCH₃ | H | (N-N triazole) | | H | H | Oil |
| 83A | 4-OCH₃ | H | (N-N pyrazole with Br) | | H | H | Oil |

-continued

General formula:

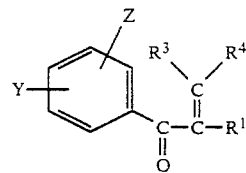

| Ex. No. | Y | Z | R¹ | R² | R³ | R⁴ | Physical constants |
|---|---|---|---|---|---|---|---|
| 84A | 4-OCH₃ | H | -N(N=CH-CH=C-Cl) pyrazole-4-Cl | H | H | H | Oil |
| 85A | 4-OCH₃ | H | -N(N=CH-CH=CH) pyrazole | H | H | H | Oil |
| 86A | 4-OCH₃ | H | -N(N=CH-C(Cl)=CH) pyrazole-3-Cl | H | H | H | Oil |
| 87A | 3-CH₃ | H | -N(N=CH-CH=C-Cl) pyrazole-4-Cl | H | H | H | Oil |
| 88A | 3-F, 4-O, 5-CF₃, (Cl) | H | -N(N=CH-CH=C-Cl) pyrazole-4-Cl | H | H | H |  |
| 89A | 4-Cl | H | -N(N=CH-CH=C-CF₃) pyrazole-4-CF₃ | H | H | H | Oil |
| 90A | 4-Cl | H | -N(N=CH-CH=C-J) pyrazole-4-J | H | H | H | Oil |
| 91A | 4-Br | H | -N(N=CH-CH=C-Br) pyrazole-4-Br | H | H | H | Oil |
| 92A | 3,4-(O-CH₂-O) dioxetane | H | -N(N=CH-CH=C-Cl) pyrazole-4-Cl | H | H | H | Oil |

-continued
General formula:
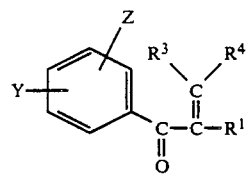
| Ex. No. | Y | Z | R¹ | R² | R³ | R⁴ | Physical constants |
|---|---|---|---|---|---|---|---|
| 93A | 3,4-O-CF₂-O | | -N-N=CH-C(Cl)= | H | H | H | Oil |
| 94A | 3,4-O-CF₂-O | | -N-N=CH-C(Br)= | H | H | H | Oil |
| 95A | 4-F | H | -N-N=CH-C(Br)= | H | H | H | Oil |
| 96A | 3,4-OCH₃ | H | -N-N=CH-C(Cl)= | H | H | H | Oil |
| 97A | 3-Cl | H | -N-N=CH-C(Cl)= | H | H | H | Oil |
| 98A | 4-OCF₂Cl | H | -N-N=CH-C(Cl)= | H | H | H | Oil |
| 99A | 4-Cl | H | -N-N=CH-CH=N | H | H | H | Oil |
| 100A₁ | 4-OCHF₂ | H | -N-N=CH-C(J)= | H | H | H | Oil |

-continued

General formula:

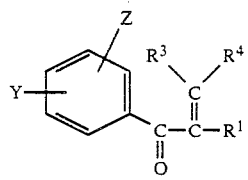

| Ex. No. | Y | Z | R¹ | R² | R³ | R⁴ | Physical constants |
|---|---|---|---|---|---|---|---|
| 100A₂ | 4-OCHF₂ | H | (N-pyrazolyl with N=, Cl, Cl substituents) | H | H | H | Oil |

EXAMPLE 101A

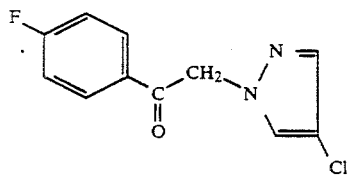

51.3 g (0.5 mol) of 4-chloropyrazole are dissolved in 700 ml of acetonitrile, and 150 g of potassium carbonate are added. 100 g of α-bromo-4-fluoroacetophenone are added to this mixture with stirring, and the mixture is refluxed for four hours, with stirring. Half of the solvent is subsequently distilled off in vacuo, 500 ml of ether are added to the residue, and the mixture is then poured into 500 ml of water.

The ether phase is separated off and dried over magnesium sulphate, and the solvent is distilled off in vacuo. 102 g of α-(1H-4-chloropyrazol-1-yl)-4'-fluoroacetophenone are obtained as a crystalline residue of melting point (M.p.) 136° C.

The following compounds can be obtained in an analogous manner:

| Ex. No. | Formula | Melting point |
|---|---|---|
| 102A | F₂HCO-C₆H₄-CO-CH₂-N(pyrazolyl) | 122–124° C. |
| 103A | F₂HCO-C₆H₄-CO-CH₂-N(1,2,3-triazolyl) | 100–102° C. |
| 104A | F₂HCO-C₆H₄-CO-CH₂-N(imidazolyl) | |
| 105A | F₂HCO-C₆H₄-CO-CH₂-N(4-chloropyrazolyl) | |
| 106A | F₃CO-C₆H₄-CO-CH₂-N(1,2,3-triazolyl) | |

-continued

| Ex. No. | Formula | Melting point |
|---|---|---|
| 107A | 4-Cl-C6H4-C(=O)-CH2-N(N=CH-CH=)Cl (pyrazole, 4-Cl) | 135–136° C. |
| 108A | 4-F3C-C6H4-C(=O)-CH2-N(N=CH-CH=)Cl (pyrazole, 4-Cl) | |
| 109A | 4-(ClFHC–CF2O)-C6H4-C(=O)-CH2-N(N=CH-CH=)Cl (pyrazole, 4-Cl) | |
| 110A | 4-(F2HCO)-C6H4-C(=O)-CH2-N(–N=CH–)C(Cl)=C(Cl)- (imidazole, 4,5-diCl) | |
| 111A | 4-(F2HCO)-C6H4-C(=O)-CH2-N(N=CH-CH=)Br (pyrazole, 4-Br) | 105° C. |
| 112A | 4-Cl-C6H4-C(=O)-CH2-N(N=CH-CH=)Br (pyrazole, 4-Br) | 134° C. |
| 113A | C6H5-C(=O)-CH2-N(N=CH-CH=)Cl (pyrazole, 4-Cl) | 148° C. |
| 114A | 4-Cl-C6H4-C(=O)-CH2-N(–N=CH–)C(CF3)=CH- (imidazole, 4-CF3) | |

| Ex. No. | Formula | Melting point |
|---|---|---|
| 115A | ![structure] | |
| 116A | ![structure] | |
| 117A | ![structure] | |
| 118A | ![structure] | |

USE EXAMPLES

In the following use examples, the compounds listed below were employed as comparison substances.

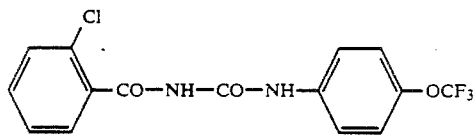

triflumuron=2-chloro-N[[[4-(trifluoromethoxy)-phenyl]amino]-carbonyl]-benzamide (disclosed in: DE-A 2,601,780)

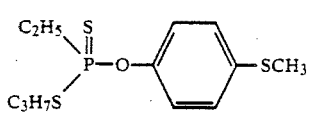

sulprofos=O-ethyl O-4-methylthiophenyl S-propyl phosphorodithioate (disclosed in: DE-A 2,111,414)

EXAMPLE A

Plutella test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (Plutella maculipennis) while the leaves are still moist.

After the desired period of time, the destruction in % is determined. 100% means that all the caterpillars have been killed; 0% means that none of the caterpillars have been killed.

In this test, a superior activity compared with the prior art is shown, for example, by the following compounds of the Preparation Examples: 1, 9, 36, 43, 45, 46, 60, 67, 102.

EXAMPLE B

Heliothis virescens test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya shoots (Glycine max) are treated by being dipped into the preparation of active compound of the desired concentration and are infested with caterpillars of the tobacco bud worm caterpillar (Heliothis virescens) while the leaves are still moist.

After the desired period of time, the destruction in % is determined. 100% means that all the caterpillars have been killed; 0% means that none of the caterpillars have been killed.

In this test, a superior activity compared with the prior art is shown, for example, by the following compounds of the Preparation Examples: 9, 23, 24, 27, 28, 29, 55, 60, 73, 74, 87, 88, 93, 94.

EXAMPLE C

LD$_{100}$ Test

Test animals: *Sitophilus granarius*
Solvent:
  35 parts by weight of ethylene glycol monomethyl ether
  35 parts by weight of nonylphenol polyglycol ether To produce a suitable formulation, three parts by weight of active compound are mixed with seven parts of the abovementioned solvent/emulsifier mixture, and the emulsion concentrate thus obtained is diluted with water to the particular desired concentration.

2 ml of this preparation of active compound are pipetted onto filter paper dishes (diameter 9.5 cm) which are located in Petri dishes of an appropriate size. After the filter disc has dried, about 30 test animals are transferred into the Petri dishes and covered.

The state of the test animals is checked 3 days after the experiments have been set up. The period which is required for a 100% knock-down effect is determined. If the LD$_{100}$ is not reached after 6 hours, the percentage of the knocked-down test animals is determined.

In this test, a highly pronounced activity is shown for example by the following compounds of the Preparation Examples: 1, 4, 9, 18, 20, 28, 29, 42, 43, 44, 45, 46, 53, 60, 62, 63, 64, 67, 69, 70, 73, 74, 77, 78, 79, 80, 82, 83, 86, 93, 94, 122, 123, 140, 145.

EXAMPLE D

Test with *Lucilia cuprina* resistant larvae
Solvent:
  35 parts by weight of ethylene glycol monomethyl ether
  35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm$^3$ of horse meat and 0.5 ml of the preparation of active compound. After 24 hours, the degree of destruction is determined.

In this test, a highly pronounced activity is shown for example by the following compounds of the Preparation Examples: 1, 4, 9, 10, 16, 17, 18, 20, 28, 36, 37, 42, 45, 46, 49, 53, 55, 60, 63, 64, 66, 67, 68, 69, 73, 74, 83, 93, 94, 104, 122, 123, 140, 145.

EXAMPLE E

LD$_{100}$ test

Test animals: *Blattella germanica*
Solvent:
  35 parts by weight of ethylene glycol monomethyl ether
  35 parts by weight of nonylphenol polyglycol ether To produce a suitable formulation, three parts by weight of active compound are mixed with seven parts of the abovementioned solvent/emulsifier mixture, and the emulsion concentrate thus obtained is diluted with water to the particular desired concentration.

2 ml of this preparation of active compound are pipetted onto filter paper dishes (0 9,5 cm) which are located in Petri dishes of an appropriate size. After the filter discs have dried, 5 test animals are transferred into the Petri dishes and covered.

The state of the test animals is checked 3 days after the experiments have been set up. The period which is required for a 100% knock-down effect is determined. If the LD$_{100}$ is not reached after 6 hours, the percentage of the knocked-down test animals is determined.

In this test, for example the compounds of Preparation Examples 4, 20, 62, 64, 67, 74, 122, 123 and 140 show a highly pronounced activity.

It is understood that the specification and examples are illustrative but not limitative of the present invention and that other embodiments within the spirit and scope of the invention will suggest themselves to those skilled in the art.

What is claimed is:

1. Substituted pyrazoline derivatives of the general formula

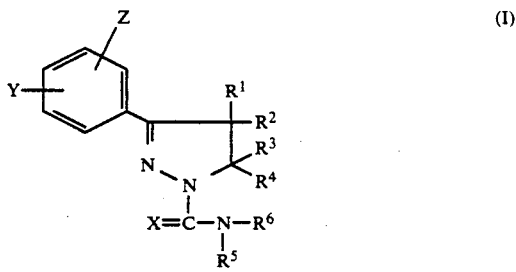

in which
  R$^1$ represents an unsaturated five-membered heterocycle which contains 1 to 4 nitrogen atoms and which is attached by way of a ring nitrogen, which is optionally substituted and which is optionally benzo-fused,
  R$^2$ represents hydrogen, alkyl, optionally substituted cycloalkyl, halogenoalkyl, halogenoalkylthio, alkoxycarbonyl or trialkylsilyl,
  R$^3$ represents hydrogen or alkyl,
  R$^4$ represents hydrogen or alkyl,
  R$^5$ represents hydrogen, alkyl, phenyl or alkylthio,
  R$^6$ represents optionally substituted alkyl or optionally substituted cycloalkyl, or represents the radical

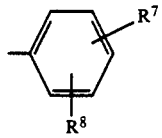

where R$^7$ and R$^8$ can be identical or different and represent hydrogen, halogen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylthionyl, alkylsulphonyl, halogenoalkylthionyl, halogenoalkylsulphonyl or halogenoalkoxycarbonyl, or where $R^7$ and $R^8$ together represent a bivalent radical which optionally contains one or two oxygen atoms and which is optionally substituted, X represents oxygen or sulphur and Y and Z can be identical or different and represent hydrogen, alkyl, halogen, halogenoalkyl, alkoxy, alkylthio, halogenoalkoxy, halogenoalkylthio, alkoxycarbonyl, halogenoalkoxycarbonyl, optionally substituted aryloxy, optionally substituted arylthio, alkenyloxy, alkinyl, alkylthionyl, alkylsulphonyl, halogenoalkylthionyl, halogenoalkylsulphonyl, amino, nitro or cyano, or where Y and Z together represent optionally halogen-substituted 3,4-methylenedioxy or 3,4-ethylenedioxy.

2. Substituted pyrazoline derivatives according to claim 1, wherein $R^1$ represents a 1H-pyrrol-1-yl, 1H-pyrazol-1-yl, 1H-imidazol-1-yl, 2H-1,2,3-triazol-2-yl, 1H-1,2,3-triazol-1-yl, 1H-1,2,4-triazol-1-yl, 4H-1,2,4-triazol-4-yl, 2H-tetrazol-2-yl or 1H-tetrazol-2-yl radical, each of which is optionally substituted by halogen, alkyl($C_1$–$C_6$), CN, $NO_2$, alkoxy($C_1$–$C_6$) carbonyl, alkyl($C_1$–$C_4$)thio, alkoxy($C_1$–$C_6$), halogenoalkyl($C_1$–$C_4$), halogenoalkyl($C_1$–$C_4$)thio, halogenoalkoxy($C_1$–$C_4$), dialkyl($C_1$–$C_4$)amino or dihalogenoamino, $R^2$ represents hydrogen, alkyl($C_1$–$C_6$), cycloalkyl($C_3$–$C_7$) which is optionally substituted by halogen or halogenoalkyl($C_1$–$C_4$); or halogenoalkyl($C_1$–$C_4$)thio, alkoxy($C_1$–$C_6$)carbonyl or trialkyl($C_1$–$C_6$)silyl, $R^3$ represents hydrogen or alkyl ($C_1$–$C_6$), $R^4$ represents hydrogen or alkyl($C_1$–$C_6$), $R^5$ represents hydrogen, alkyl($C_1$–$C_6$), phenyl or alkyl ($C_1$–$C_4$)thio, $R^6$ represents alkyl($C_1$–$C_6$) which is optionally substituted by halogen, halogenoalkyl($C_1$–$C_4$) or halogenoalkoxy($C_1$–$C_4$), or represents cycloalkyl ($C_3$–$C_7$) which is optionally substituted by halogen, halogenoalkyl ($C_1$–$C_4$), halogenoalkoxy($C_1$–$C_4$), or represents the radical

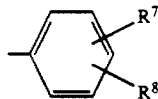

where $R^7$ and $R^8$ can be identical or different and represent hydrogen, halogen, alkyl($C_1$–$C_6$), nitro, cyano, halogenoalkyl($C_1$–$C_6$), alkoxy($C_1$–$C_6$), halogenoalkoxy($C_1$–$C_6$), alkyl($C_1$–$C_6$)thio, halogenoalkyl($C_1$–$C_4$)thio, phenoxy or phenylthio each of which is optionally substituted by halogen, halogenoalkyl($C_1$–$C_6$), alkoxy($C_1$–$C_6$) or alkyl($C_1$–$C_6$), or represent mono- or dialkylamino each of which has 1 to 6 carbon atoms in the alkyl radical and each of which is optionally substituted by halogen, alkoxy($C_1$–$C_4$) or halogenoalkyl($C_1$–$C_4$), or represent cycloalkyl($C_3$–$C_7$) which is optionally substituted by alkyl ($C_1$–$C_4$), alkoxy($C_1$–$C_4$), halogen or alkyl($C_1$–$C_4$)thio, or represent alkoxy($C_1$–$C_6$)carbonyl, alkenyl($C_2$–$C_6$)oxy, alkinyl($C_2$–$C_6$), alkyl($C_1$–$C_4$)thionyl, alkyl($C_1$–$C_4$)sulphonyl, halogenoalkyl($C_1$–$C_4$)-thionyl or halogenoalkyl($C_1$–$C_4$)sulphonyl, or where $R^7$ and $R^8$ together represent one of the following bivalent radicals:

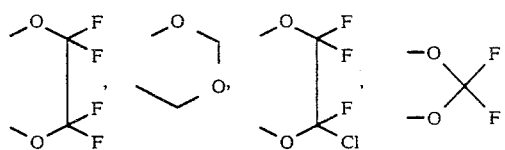

X represents oxygen or sulphur and Y and Z can be identical or different and represent hydrogen, alkyl($C_1$–$C_6$), halogen, halogenoalkyl($C_1$–$C_6$), alkoxy($C_1$–$C_6$), alkyl($C_1$–$C_6$)thio, halogenoalkoxy($C_1$–$C_4$), halogenoalkyl($C_1$–$C_4$)thio, alkoxy($C_1$–$C_4$)carbonyl, phenoxy or phenylthio each of which is optionally substituted by halogen, alkyl($C_1$–$C_4$), alkoxy($C_1$–$C_4$) or halogenoalkyl ($C_1$–$C_4$), or represent alkenyl($C_2$–$C_6$)oxy, alkinyl($C_2$–$C_6$), alkyl($C_1$–$C_4$)thionyl, alkyl($C_1$–$C_4$)sulphonyl, halogenoalkyl($C_1$–$C_4$)thionyl, halogenoalkyl($C_1$–$C_4$)sulphonyl, mono- or dialkyl($C_1$–$C_6$)amino each of which is optionally substituted by halogen, alkoxy($C_1$–$C_4$) or halogenoalkyl($C_1$–$C_4$), or represent nitro or cyano, or where Y and Z together represent optionally fluorine- and/or chlorine-substituted 3,4-methylenedioxy or 3,4-ethylenedioxy.

3. Substituted pyrazoline derivatives according to claim 1, wherein $R^1$ represents a 1H-pyrrol-1-yl, 1H-pyrazol-1-yl, 1H-imidazol-1-yl, 2H-1,2,3,-triazol-2-yl, 1H-1,2,3-triazol-1-yl, 1H-1,2,4-triazol-1-yl, 4H-1,2,4-triazol-4-yl, 1-H-1,2,4-triazolyl-(1), 4-H-1,2,4-triazolyl-(4)-, 2H-tetrazol-2-yl or 1H-tetrazol-1-yl radical, each of which is optionally substituted by fluorine, chlorine, bromine, iodine, alkyl($C_1$–$C_4$), CN, $NO_2$, alkoxy($C_1$–$C_4$)carbonyl, alkyl($C_1$–$C_3$) thio, alkoxy($C_1$–$C_4$), halogenoalkyl($C_1$–$C_3$), halogenoalkyl($C_1$–$C_3$)thio or halogenoalkoxy($C_1$–$C_4$) carbonyl, $R^2$ represents hydrogen, alkyl($C_1$–$C_4$), optionally fluorine-, chlorine-, bromine- or halogenoalkyl ($C_1$–$C_3$)-substituted cycloalkyl($C_3$–$C_6$), halogenoalkyl($C_1$–$C_3$), halogenoalkyl($C_1$–$C_3$)thio, alkoxy ($C_1$–$C_4$)-carbonyl or trialkyl($C_1$–$C_4$)silyl, $R^3$ represents hydrogen or alkyl($C_1$–$C_4$), $R^4$ represents hydrogen or alkyl($C_1$–$C_4$), $R^5$ represents hydrogen, alkyl($C_1$–$C_4$), phenyl or alkyl($C_1$–$C_3$)thio, $R^6$ represents alkyl($C_1$–$C_4$) which is optionally substituted by fluorine, chlorine, bromine, halogenoalkyl($C_1$–$C_3$) or halogenoalkoxy($C_1$–$C_3$), or represents cycloalkyl($C_3$–$C_6$) which is optionally substituted by fluorine, chlorine, bromine, halogenoalkyl($C_1$–$C_3$) or halogenoalkoxy($C_1$–$C_3$), or represents the radical

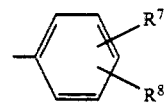

where $R^7$ and $R^8$ can be identical or different and represent hydrogen, fluorine, chlorine, bromine, iodine, alkyl($C_1$–$C_4$), nitro, cyano, halogenoalkyl($C_1$–$C_3$), alkoxy($C_1$–$C_4$), halogenoalkoxy ($C_1$–$C_3$), alkyl($C_1$–$C_3$)thio, halogenoalkyl($C_1$–$C_3$)thio, or phenoxy which is optionally substituted by fluorine, chlorine, bromine, halogenoalkyl($C_1$–$C_3$), alkoxy($C_1$–$C_3$) or alkyl($C_1$–$C_3$), or represent monoor dialkylamino each of which has 1 to 4 carbon atoms in the alkyl radical and each of which is optionally substituted by fluorine, chlorine, bromine, alkoxy($C_1$-$C_3$) or halogenoalkyl($C_1$-$C_3$), or represent cycloalkyl($C_3$-$C_6$) which is optionally substituted by alkyl($C_1$-$C_3$), alkoxy($C_1$-$C_3$), fluorine, chlorine, bromine or alkyl($C_1$-$C_3$)thio, or where $R^7$ and $R^8$ together represent one of the following bivalent radical:

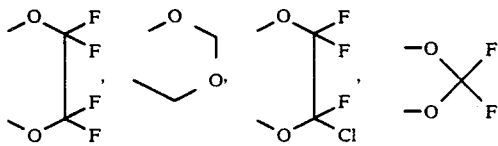

X represents oxygen or sulphur and Y and Z can be identical or different and represent hydrogen, alkyl($C_1$-$C_4$), fluorine, chlorine, bromine, iodine, halogenoalkyl($C_1$-$C_4$), alkoxy($C_1$-$C_4$), alkyl($C_1$-$C_4$)thio, halogenoalkoxy($C_1$-$C_3$), halogenoalkyl($C_1$-$C_3$)thio, alkoxy($C_1$-$C_3$)carbonyl, phenoxy or phenylthio each of which is optionally substituted by fluorine, chlorine, bromine, alkyl($C_1$-$C_3$), alkoxy ($C_1$-$C_3$) or halogenoalkyl($C_1$-$C_3$), or represent halogenoalkoxy($C_1$-$C_3$)carbonyl, alkenyl($C_2$-$C_4$)oxy, alkinyl($C_2$-$C_4$), alkyl($C_1$-$C_3$) thionyl, alkyl($C_1$-$C_3$)sulphonyl, halogenoalkyl $C_1$-$C_3$)thionyl, halogenoalkyl($C_1$-$C_3$)sulphonyl, nitro or cyano, or where Y and Z together represent optionally fluorine- and/or chlorine-substituted 3,4-methylenedioxy or 3,4-ethylenedioxy.

4. Pesticidal compositions, characterized in that they contain at least one substituted pyrazoline derivative according to claim 1.

5. Method of combating animal pests, characterized in that substituted pyrazoline derivatives according to claim 1 are allowed to act on animal pests and/or their environment.

* * * * *